(12) United States Patent
Meijs et al.

(10) Patent No.: US 6,627,724 B2
(45) Date of Patent: *Sep. 30, 2003

(54) POLYSILOXANE-CONTAINING POLYURETHANE ELASTOMERIC COMPOSITIONS

(75) Inventors: Gordon Francis Meijs, Murrumbeena (AU); Pathiraja Arachchillage Gunatillake, Mulgrave (AU); Simon John McCarthy, Forest Hill (AU)

(73) Assignee: Aortech Biomaterials PTY LTD, Chastwood (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/736,587

(22) Filed: Dec. 13, 2000

(65) Prior Publication Data

US 2003/0018156 A1 Jan. 23, 2003

Related U.S. Application Data

(62) Division of application No. 09/147,971, filed as application No. PCT/AU97/00619 on Sep. 19, 1997, now Pat. No. 6,313,254.

(30) Foreign Application Priority Data

Sep. 23, 1996 (AU) .............................................. PO2510

(51) Int. Cl.[7] ........................................... C08G 77/458
(52) U.S. Cl. .................... 528/26; 528/28; 428/423.1; 428/904; 428/15
(58) Field of Search ................. 528/26, 28; 428/423.1, 428/904, 15

(56) References Cited

U.S. PATENT DOCUMENTS

| | | | |
|---|---|---|---|
| 3,246,048 A | * 4/1966 | Haluska | 528/28 |
| 3,804,786 A | 4/1974 | Sekmakas | 260/18 PT |
| 3,826,768 A | 7/1974 | Suzuki et al. | 260/26.2 TN |
| 3,852,090 A | 12/1974 | Leonard et al. | 117/14 |
| 4,124,572 A | 11/1978 | Mao | 528/76 |
| 4,183,836 A | 1/1980 | Wolfe, Jr. | 260/29.2 TN |
| 4,190,566 A | 2/1980 | Noll et al. | 260/29.2 TN |
| 4,202,480 A | 5/1980 | Fildes et al. | 424/78 |
| 4,202,957 A | 5/1980 | Bonk et al. | 528/77 |
| 4,224,432 A | 9/1980 | Pechhold et al. | 528/76 |
| 4,367,327 A | 1/1983 | Holker et al. | 528/61 |
| 4,528,343 A | 7/1985 | Kira | 528/26 |
| 4,530,974 A | 7/1985 | Munro et al. | 525/329.4 |
| 4,631,329 A | 12/1986 | Goronowicz et al. | 528/28 |
| 4,647,643 A | * 3/1987 | Zdrahala et al. | 528/28 |
| 4,663,413 A | 5/1987 | Ward et al. | 528/26 |
| 4,675,361 A | * 6/1987 | Ward, Jr. | 525/92 |
| 4,686,137 A | 8/1987 | Ward, Jr. et al. | 428/290 |
| 4,719,277 A | 1/1988 | Behnke et al. | 528/48 |
| 4,743,629 A | 5/1988 | Karakelle et al. | 521/175 |
| 4,849,458 A | 7/1989 | Reed et al. | 521/159 |
| 4,861,830 A | 8/1989 | Ward, Jr. | 525/92 |
| 4,892,538 A | 1/1990 | Aebischer et al. | 604/891.1 |
| 4,963,595 A | 10/1990 | Ward et al. | 525/415 |
| 4,973,320 A | 11/1990 | Brenner et al. | 604/265 |
| 5,017,664 A | 5/1991 | Grasel et al. | 525/454 |
| 5,047,456 A | 9/1991 | Onwumere et al. | 524/13 |
| 5,070,169 A | 12/1991 | Robertson et al. | 528/25 |
| 5,079,168 A | 1/1992 | Amiot | 437/284 |
| 5,109,077 A | 4/1992 | Wick | 525/467 |
| 5,133,742 A | 7/1992 | Pinchuk | 623/1 |
| 5,221,724 A | 6/1993 | Li et al. | 528/28 |
| 5,235,003 A | 8/1993 | Ward et al. | 525/476 |
| 5,428,123 A | 6/1995 | Ward et al. | 128/28 |
| 5,430,121 A | * 7/1995 | Pudleiner et al. | 528/28 |
| 5,589,563 A | 12/1996 | Ward et al. | 528/44 |
| 5,777,060 A | * 7/1998 | Van Antwerp | 528/28 |
| 5,863,627 A | * 1/1999 | Szycher et al. | 428/36.8 |
| 6,313,254 B1 | * 11/2001 | Meijs et al. | 528/26 |

FOREIGN PATENT DOCUMENTS

| | | | |
|---|---|---|---|
| AU | 80065/91 | 1/1992 | A61L/17/00 |
| EP | 0107915 | 5/1984 | A61F/13/02 |
| EP | 0272682 | 6/1988 | C08G/81/00 |
| EP | 0302186 | 2/1989 | A61L/29/00 |
| EP | 0333899 | 9/1989 | C08G/18/08 |
| EP | 0603679 | 6/1994 | C08G/18/65 |
| GB | 2049544 | 12/1980 | B01D/13/00 |
| GB | 2073219 | 10/1981 | C08L/75/04 |
| JP | 60-236658 | 11/1985 | A61L/33/00 |
| JP | 4248826 A | 9/1992 | C08G/18/83 |
| WO | 85/05322 | 12/1985 | B32B/27/40 |
| WO | 85/05373 | 12/1995 | C08L/75/04 |
| WO | 98/13405 | 4/1998 | C08G/18/44 |

OTHER PUBLICATIONS

*Patent Abstracts of Japan*, Publication No. 08282866 A, pp. 1–2, (May 20, 1996).

*Patent Abstracts of Japan*, Publication No. 05279447, 1 p., (Oct. 26, 1993).

*Patent Abstracts of Japan*, Publication No. 02041325, 1 p., (Feb. 9, 1990).

*Patent Abstracts of Japan*, Publication No. 63179916, 1 p., (Jul. 23, 1988).

(List continued on next page.)

*Primary Examiner*—Margaret G. Moore
(74) *Attorney, Agent, or Firm*—Schwegman, Lundberg, Woessner & Kluth, P.A.

(57) ABSTRACT

The present invention relates to a material having improved mechanical properties, clarity, processability and/or degradation resistance comprising a polyurethane elastomeric composition which includes a soft segment derived from at least one polysiloxane macrodiol and at least one polyether and/or polycarbonate macrodiol. This material can function as a degradation-resistant material or biomaterial and is particularly useful in the manufacture of medical devices, articles or implants which contact living tissue or bodily fluids. The present invention also provides a polyurethane elastomeric composition which includes a soft segment derived from at least one polysiloxane and at least one polyether and/or polycarbonate macrodiol and processes for its preparation.

43 Claims, 8 Drawing Sheets

OTHER PUBLICATIONS

Chen, C.T., et al., "Synthesis, Characterization, and Permeation Properties of Polyether–Based Polyurethanes", *Journal of Applied Polymer Science, 16*, pp. 2105–2114, (1972).

Farrar, D.J., et al., "In vivo evaluations of a new thromboresistant polyurethane for artificial heart blood pumps", *The Journal of Thoracic and Cardiovascular Surgery, 95*(2), pp. 191–200, (Feb. 1988).

Grasel, T.G., et al., "Surface properties and blood compatibility of polyurethaneureas", *Biomaterials, 7*, pp. 315–328, (Sep. 1986).

Hergenrother, R.W., et al., "Blood–contacting properties of polydimethylsiloxane polyurea–urethanes", *Biomaterials, 15* (8), pp. 635–640, (1994).

Lim, F., et al., "Synthesis, characterization and ex vivo evaluation of polydimethylsiloxane polyurea–urethanes", *Biomaterials, 15* (6), pp. 408–416, (1994).

Nyilas, E., et al., "Development of Blood–Compatible Elastomers. V. Surface Structure and Blood Compatibility of Avcothane Elastomers", *In: Biological Interactions at Polymer Surfaces*, Journal of Biomedical Materials Research, Biomedical Materials Symposium, No. 8, John Wiley & Sons, Inc., NY, pp. 69–84, (1977).

Okkema, A.Z., et al., "Bulk, surface, and blood–contacting properties of polyetherurethanes modified with polyethylele oxide", *J. Biomater. Sci. Polymer Edn, 1* (1), pp. 43–62, (1989).

Paynter, R.W., et al., "The Hydrolytic stability of Mitrathane (a polyurethane urea)—an x-ray photoelectron spectroscopy study", *Journal of Biomedical Materials Research, 22* (7), pp. 687–698, (Jul. 1988).

Philips, R.A., et al., "Structure–Property Relationships and Mositure Sensitivity of PDMS/PTMO Mixed Soft Segment Urethane Elastomers", *J. Macromol. Sci.—Phys., B27* (2&3), pp. 245–274 (1988).

Sakurai, S., et al., "Changes in Structure and Properties due to Mechanical Fatigue for Polyurethanes Containing Poly-(dimethyl siloxane)", *Polymer, 35* (3), pp. 532–539 (1994).

Speckhard, T.A., et al., "Ultimate Tensile Properties of Segmented Polyurethane Elastomers: Factors Leading to Reduced Properties for Polyurethanes Based on Nonpolar Soft Segments", *Rubber Chemistry and Technology, 59*, pp. 405–429, (1986).

Szycher, M., et al., "Blood Compatible Polyurethane Elastomers", *Journal of Biomaterials Applications, 2*, pp. 290–313, (Oct. 1987).

Takahara, A., et al., "Effect of soft segment chemistry on the biostability of segmented polyurethanes. II. In vitro hydrolytic degradation and lipid sorption", *Journal of Biomedical Materials Research, 26*, pp. 801–818, (1992).

Takahara, A., et al., "Surface molecular mobility and platelet reactivity of segmented poly(etherurethaneuraneas) with hydrophilic and hydrophobic soft segment components", *J. Biomater. Sci. Polymer Edn, 1*(1), pp. 17–29, (1989).

Turner, A.P., et al., *Biosensors–Fundamentals and Applications*, Turner, A.P.F., et al., (editors), Oxford University Press, Exhibit 2, pp. 368–369, (1987).

Ward, R.S., "Surface Modification Prior to Surface Formation: Control of Polymer Surface Properties via Bulk Composition", *Medical Plastics and Biomaterials*, Materials Forum, pp. 34–41, (1995).

Ward, R.S., "Surface Modifying Additives for Biomedical Polymers", *IEEE Engineering in Medicine and Biology Magazine*, pp. 22–25, (Jun. 1989).

Ward, R.S., et al., "A Thromboresistant Silicone–Urethane Catheter Compound With 100 Fold Modulus Reduction Following Insertion", *MD&DI 85 West Proceedings, Poster #314*, pp. 72–74.

Ward, R.S., et al., "BPS–215M: A Polyurethaneurea for Biomedical Devices: Development and In Vivo Testing in the Pierce–Donachy VAD", *The 13th Annual Meeting of the Society for Biomaterials*, New York, New York USA, p. 259, (Jun. 2–6, 1987).

Ward, R.S., et al., "Development of a Hybrid Artificial Pancreas with a Dense Polyurethane Membrane", *ASAIO Journal, 39*(3), pp. M261–M267, (1993).

Ward, R.S., et al., "Development of a New Family of Polyurethaneurea Biomaterials", *Proceedings from the Eighth Cimtec—Forum on New Materials Topical Symposium VIII, Materials in Clinical Applications*, Florence, Italy, 8 p., (Jul. 1994).

Ward, R.S., et al., "Development of Biostable Thermoplastic Polyurethanes with Oligomeric Polydimethylsiloxane End Groups", *Proceedings of the 21st Annual Meeting of the Society for Biomaterials*, San Francisco, CA, p. 268, (Mar. 18–22, 1995).

Ward, R.S., et al., "Improved Polymer Biostability Via Oligomeric End Groups Incorporated During Synthesis", *Polymeric Materials Science and Engineering, 79*, Fall Meeting, Boston, Mass., pp. 526–527, (Aug. 23–27, 1998).

Ward, R.S., et al., "Polymers with Stepwise–Variable Surface Chemistry: Comparison of IR+ Visible Sum Frequency Generation to Contact Angle Goniometry", *24th Annual Meeting of the Society for Biomaterials*, San Diego, CA, p. 532, (Apr. 22–26, 1998).

Ward, R.S., et al., "Production of Biomedical Polymers I. Silicone/Urethane Synergy in Avocathane R Elastomers" *In: Organometallic Polymers*, Edited by Charles E. Carraher, Jr., Published by Academic Press, NY, pp. 219–229, (1978).

Ward, R.S., et al., "Surface Activity and Enhanced In Vivo Biostability of a Segment Polyetherurethane with Polydimethysiloxane End Groups", *Proceedings of the Fifth World Biomaterials Congress*, Toronto, Canada, p. 818, (May 29–Jun. 2, 1996).

Ward, R.S., et al., "Thermoplastic Siloxane–Urethane Block Copolymers and Terpolymers for Biomedical Use", *Proceedings of the Third World Biomaterials Congress*, Kyoto, Japan, p. 433, (Apr. 21–25, 1988).

Ward, R.S., et al., "Use of Infrared–Visible Sum Frequency Generation to Characterize Surfaces of Segmented Polyurethanes With Surface–Modifying End Groups", *23rd Annual Meeting of the Society for Biomaterials*, New Orleans, LA, p. 122, (Apr. 30–May 4, 1997).

Ward, R.S., et al., "Use of Ogliomeric End–Groups to Modify Surface Properties of Biomedical Polymers", *Proceedings of the 20th Annual Meeting of the Society for Biomaterials*, Boston, MA, p. 13, (Apr. 5–9, 1994).

Ward, R.S., et al., "Use of Surface–Modifying Additives in the Development of a New Biomedical Polyurethaneurea", *Polyurethanes in Biomedical Engineering*, H. Planek et al. (editors), Elsevier Science Publishers B.V., Amsterdam, pp. 181–200, (1984).

White, K.A., et al., "In Vivo Evaluation of Polyurethanes", *24th Annual Meeting of the Society for Biomaterials,* San Diego, CA, p. 385, (Apr. 22–26, 1998).

White, K.A., et al., "Surface Modification of Segmented Polyurethaneureas via Oligomeric End Groups Incorporated During Synthesis", *In: Surface Modification of Polymeric Biomaterials,* Edited by B.D. Rainer et al., Plenum Press, New York, NY, pp. 27–33, (1996).

White, K.A., et al., "Synthesis and Characterization of Three Polyurethanureas for Use as Primary Reference Materials", *The Third World Biomaterials Congress,* Kyoto, Japan, p. 431, (Apr. 21–25, 1988).

Wise, D.L., et al., *Biosenosrs with Fiberoptics,* Wise, D.L.,. et al., (editors), Humana Press, Exhibit 1, pp. 326–327, (1991).

Yoon, S.C., et al., "Surface and Bulk Structure of Segmented Poly(ether urethanes) with Perfluoro Chain Extenders. 5. Incorporation of Poly(dimethylsiloxane) and Polyisobutylene Macroglycols", *Macromolecules,* 27 (6), pp. 1548–1554, (1994).

* cited by examiner

POLYSILOXANE-CONTAINING POLYURETHANE ELASTOMERIC COMPOSITIONS

This application is a Divisional of application Ser. No. 09/147,971, filed on May 17, 1999, now U.S. Pat. No. 6,313,254, which in turn is a national stage application filing of International application No. PCT/AU97/00619, filed Sep. 19, 1997, which in turn claims the benefit of Australian application No. PO 2510, filed Sep. 23, 1996, all of which are incorporated herein by reference.

The present invention relates to polysiloxane-containing polyurethane elastomeric compositions having improved properties which make them useful for a variety of applications, in particular the manufacture of medical devices, articles or implants which contact living tissues or bodily fluids.

Polyurethane elastomers represent an important class of segmented copolymers with excellent mechanical properties including high tensile strength, good tear and abrasion resistance and a relatively good stability in biological environments. Accordingly, polyurethanes are widely used in medical implants such as cardiac pacemakers, catheters, implantable prostheses, cardiac assist devices, heart valves and vascular grafts. The excellent mechanical properties of segmented polyurethanes are attributed to their two phase morphology derived from microphase separation of soft and hard segments. In polyurethanes used for long term medical implants, the soft segments are typically formed from a polyether macrodiol such as polytetramethylene oxide (PTMO) whereas the hard segments are derived from a diisocyanate such as 4,4'-methylenediphenyl diisocyanate (MDI) and a diol chain extender such as 1,4-butanediol.

Although PTMO-based polyurethanes are the materials of choice for a wide variety of medical implants, in some cases the polyurethanes degrade causing malfunction or failure of the implant. Degradation is usually apparent in terms of surface or deep cracking, stiffening, erosion or the deterioration of mechanical properties such as flexural strength[1]. The mechanisms responsible for such degradations include environmental stress cracking, the generation of cracks and crazes produced by the medium acting on the polyurethane at certain stress levels and metal ion induced oxidation. It is generally accepted that ether linkages in the PTMO-based elastomers are the most vulnerable sites for initiation of degradations[2]. Efforts have been made to overcome this problem by developing polyurethanes that are not exclusively based on PTMO such as those disclosed in Australian Patent No. 657267, U.S. Pat. No. 4,875,308 (Courey et al), U.S. Pat. No. 5,133,742 (Pinchuck) and U.S. Pat. No. 5,109,077 (Wick). Nevertheless, the combination of degradation resistance, mechanical characteristics, processability and clarity is suboptimal for certain applications. For example, there has been a long felt need for polyurethanes combining low durometer hardness, high flexibility, good processability and high resistance to degradation within the pacing industry for the insulation of leads. With the polyurethanes described in the aforementioned patents, there appears to be a lower limit to flexibility and Shore hardness, below which degradation resistance and/or mechanical properties are adversely affected.

Polycarbonate macrodiols have also been used as reactive ingredients in the synthesis of block and segmented copolymer systems, in particular high performance polyurethanes. Processes for preparing polycarbonate macrodiols based on a range of bishydroxy alkylene compounds are disclosed in JP 62,241,920 (Toa Gosei Chemical Industry Co. Ltd.), JP 64,01,726 (Dainippon Ink and Chemicals, Inc.), JP 62,187,725 (Daicel Chemical Industries, Ltd.), DE 3,717,060 (Bayer A. G.), U.S. Pat. No. 4,105,641 (Bayer Aktiengesellschaft), U.S. Pat. No. 4,131,731 (Beatrice Foods Company) and U.S. Pat. No. 5,171,830 (Arco Chemical Technology).

Polysiloxane-based materials, especially polydimethyl siloxane (PDMS) exhibit characteristics such as low glass transition temperatures, good thermal, oxidative and hydrolytic stabilities, low surface energy, good haemocompatibility and low toxicity. They also display an improved ability to be bonded to silicone components, by such procedures as gluing, solvent welding, coextrusion or comolding. For these reasons PDMS has been used in biomedical applications[3,4]. However, PDMS-based polymers generally have limitations and do not exhibit the necessary combination of tear resistance, abrasion resistance and tensile properties for many types of implants intended for long term use. It would be desirable for polymers to be available with the stability and biological properties of PDMS, but the strength, abrasion resistance, processability and other physical properties of polyurethanes. Polyurethanes incorporating PDMS would appear to fulfil this need, but to date, despite much experimentation, no compositions have been produced with the optimal combination of physical and biological properties.

Previous attempts to incorporate PDMS into polyurethanes have not been very successful[5]. Speckhard et al[6] have indicated that as a result of the large differences in solubility parameters between polysiloxane and hard segments, PDMS-based polyurethanes are likely to be highly phase separated materials having poor mechanical properties. As a consequence of a large difference in polarity between hard and soft segments, it is anticipated that premature phase separation will occur during synthesis leading to compositional heterogenity and a low molecular weight. This is borne out by experiment and typically the tensile strength and elongation at break of PDMS-based polyurethanes is about 7 MPa and 200%, respectively[6].

Several techniques have been reported in the literature to improve mechanical properties of PDMS-based polyurethanes with the primary focus being increasing the interfacial adhesion between soft PDMS phase and hard segments. These include mixing with certain polyethers or polyesters[7], (b) introduction of polar functionality to PDMS (c) use of copolymers of PDMS and polyethers as soft segments and (d) hard segment modifications. Only marginal improvements in mechanical properties have been observed using these techniques.

A requirement accordingly exists to develop methods for incorporating polysiloxane segments as part of the polyurethane structure to yield materials with good mechanical properties. The current demand for materials with improved biocompatibility and stability warrants development of polysiloxane-containing polyurethanes, especially those that are resistant to degradation when implanted for long periods of time.

According to the present invention there is provided a material having improved mechanical properties, clarity, processability and/or degradation resistance comprising a polyurethane elastomeric composition which includes a soft segment derived from a polysiloxane macrodiol and a polyether and/or polycarbonate macrodiol.

It will be appreciated that more than one polysiloxane macrodiol and polyether and/or polycarbonate macrodiol may be present in the polyurethane elastomeric composition.

The present invention also provides use of the polyurethane elastomeric composition defined above as a material having improved mechanical properties, clarity, processability and/or degradation resistance.

The present invention further provides the polyurethane elastomeric composition defined above when used as a material having improved mechanical properties, clarity, processability and/or degradation resistance.

The mechanical properties which are improved include tensile strength, tear strength, abrasion resistance, Durometer hardness, flexural modulus and related measures of flexibility.

The improved resistance to degradation includes resistance to free radical, oxidative, enzymatic and/or hydrolytic processes and to degradation when implanted as a biomaterial.

The improved processability includes ease of processing by casting such as solvent casting and by thermal means such as extrusion and injection molding, for example, low tackiness after extrusion and relative freedom from gels.

There is also provided a degradation resistant material which comprises the polyurethane elastomeric composition defined above.

The polyurethane elastomeric composition of the present invention shows significantly improved degradation resistance over the softer grades disclosed in U.S. Pat. No. 4,875,308 and the commercially available polyurethane Pellethane 2363-80A (Registered Trade Mark). It also has a good compatibility and stability in biological environments, particularly when implanted in vivo for extended periods of time.

According to another aspect of the present invention there is provided an in vivo degradation resistant material which comprises the polyurethane elastomeric composition defined above.

The polyurethane elastomeric composition may also be used as a biomaterial. The term "biomaterial" is used herein in its broadest sense and refers to a material which is used in situations where it comes into contact with the cells and/or bodily fluids of living animals or humans.

The polyurethane elastomeric composition is therefore useful in manufacturing medical devices, articles or implants.

Thus, the present invention still further provides medical devices, articles or implants which are composed wholly or partly of the polyurethane elastomeric composition defined above.

It will be understood that the polyurethane elastomeric composition may be used as a coating on medical devices, articles or implants.

The medical devices, articles or implants may include cardiac pacemakers and defibrillators, catheters, cannulas, implantable prostheses, cardiac assist devices, heart valves, vascular grafts, extra-corporeal devices, artificial organs, pacemaker leads, defibrillator leads, blood pumps, balloon pumps, A-V shunts, biosensors, membranes for cell encapsulation, drug delivery devices, wound dressings, artificial joints, orthopaedic implants and soft tissue replacements.

It will be appreciated that polyurethane elastomeric compositions having properties optimised for use in the construction of various medical devices, articles or implants will also have other non-medical applications. Such applications may include their use in the manufacture of artificial leather, shoe soles; cable sheathing; varnishes and coatings; structural components for pumps, vehicles, etc.; mining ore screens and conveyor belts; laminating compounds, for example in glazing; textiles; separation membranes; sealants or as components of adhesives.

Thus, the present invention extends to the use of the polyurethane elastomeric composition defined above in the manufacture of devices or articles.

The present invention also provides devices or articles which are composed wholly or partly of the polyurethane elastomeric composition defined above.

Some of the polyurethane elastomeric compositions of the present invention are novel per se. These novel compositions exhibit unexpectedly improved clarity, processability, flexural modulus, mechanical properties, abrasion resistance, softness and/or resistance to degradation which make them suitable for a wide range of applications.

Thus, the present invention further provides a polyurethane elastomeric composition which includes macrodiols derived from 60 to 98 wt %, more preferably 70 to 90 wt % of a polysiloxane macrodiol and 2 to 40 wt %, more preferably 10 to 30 wt % of a polyether and/or polycarbonate macrodiol.

Suitable polysiloxane macrodiols are hydroxy terminated and include those represented by the formula (I)

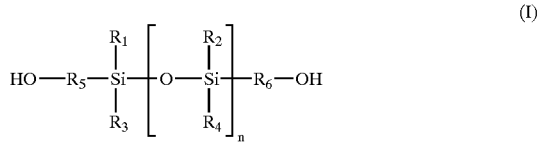

wherein
$R_1$, $R_2$, $R_3$, $R_4$, $R_5$ and $R_6$ are same or different and selected from an optionally substituted straight chain, branched or cyclic, saturated or unsaturated hydrocarbon radical; and
n is an integer of 1 to 100.

A preferred polysiloxane is PDMS which is a compound of formula (I) wherein $R_1$ to $R_4$ are methyl and $R_5$ and $R_6$ are as defined above. Preferably $R_5$ and $R_6$ are the same or different and selected from propylene, butylene, pentylene, hexylene, ethoxypropyl (—$CH_2CH_2OCH_2CH_2CH_2$—), propoxypropyl and butoxypropyl.

The hydrocarbon radical for substituents $R_1$, $R_2$, $R_3$ and $R_4$, may include alkyl, alkenyl, alkynyl, aryl or heterocyclyl radicals. It will be appreciated that the equivalent radicals may be used for substituents $R_5$ and $R_6$ except that the reference to alkyl, alkenyl and alkynyl should be to alkylene, alkenylene and alkynylene, respectively. In order to avoid repetition, only detailed definitions of alkyl, alkenyl and alkynyl are provided hereinafter.

The term "alkyl" denotes straight chain, branched or mono- or poly-cyclic alkyl, preferably $C_{1-12}$ alkyl or cycloalkyl. Examples of straight chain and branched alkyl include methyl, ethyl, propyl, isopropyl, butyl, isobutyl, sec-butyl, tert-butyl, amyl, isoamyl, secamyl, 1,2-dimethylpropyl, 1,1-dimethylpropyl, pentyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-prophylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl 1-, 2-, 3-, 4-, 5-, 6,7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1,2-pentylheptyl and the like. Examples of cyclic alkyl include cyclopropyl, cyclobutyl, cyclopentyl, cyclohexyl, cycloheptyl, cyclooctyl, cyclononyl and cyclodecyl and the like.

The term "alkenyl" denotes groups formed from straight chain, branched or mono- or poly-cyclic alkenes including ethylenically mono- or poly-unsaturated alkyl or cycloalkyl groups as defined above, preferably $C_{2-12}$ alkenyl. Examples of alkenyl include vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4, pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-cycloocta-tetraenyl and the like.

The term "alkynyl" denotes groups formed from straight chain, branched, or monoor poly-cyclic alkynes. Examples of alkynyl include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl, 3-octadecynyl and the like.

The term "aryl" denotes single, polynuclear, conjugated and fused residues of aromatic hydrocarbons. Examples of aryl include phenyl, biphenyl, terphenyl, quaterphenyl, phenoxyphenyl, naphthyl, tetrahydronaphthyl, anthracenyl, dihydroanthracenyl, benzanthracenyl, dibenzanthracenyl, phenanthrenyl and the like.

The term "heterocyclyl" denotes mono- or poly-cyclic heterocyclyl groups containing at least one heteroatom atom selected from nitrogen, sulphur and oxygen. Suitable heterocyclyl groups include N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl; saturated 3 to 6-membered heteromonocyclic groups containing 1 to 4 nitrogen atoms, such as pyrrolidinyl, imidazolidinyl, piperidino or piperazinyl; unsaturated condensed heterocyclic groups containing 1 to 5 nitrogen atoms, such as, indolyl, isoindolyl, indolizinyl, benzimidazolyl, quinolyl, isoquinolyl, indazolyl, benzotriazolyl or tetrazolopyridazinyl; unsaturated 3 to 6-membered heteromonocyclic group containing an oxygen atom, such as, pyranyl or furyl; unsaturated 3 to 6-membered heteromonocyclic group containing 1 to 2 sulphur atoms, such as, thienyl; unsaturated 3 to 6-membered heteromonocydic group containing 1 to 2 oxygen atoms and 1 to 3 nitrogen atoms, such as, oxazolyl, isoxazolyl or oxadiazolyl; saturated 3 to 6-membered heteromonocyclic group containing 1 to 2 oxygen atoms and 1 to 3 nitrogen atoms, such as, morpholinyl; unsaturated condensed heterocyclic group containing 1 to 2 oxygen atoms and 1 to 3 nitrogen atoms, such as, benzoxazolyl or benzoxadiazolyl; unsaturated 3 to 6-membered heteromonocyclic group containing 1 to 2 sulphur atoms and 1 to 3 nitrogen atoms, such as, thiazolyl or thiadiazolyl; saturated 3 to 6-membered heteromonocy-clic group containing 1 to 2 sulphur atoms and 1 to 3 nitrogen atoms, such as, thiadiazolyl; and unsaturated condensed heterocyclic group containing 1 to 2 sulphur atoms and 1 to 3 nitrogen atoms, such as benzothiazolyl or benzothiadiazolyl.

In this specification, "optionally substituted" means that a group may or may not be further substituted with one or more groups selected from oxygen, nitrogen, sulphur, alkyl, alkenyl, alkynyl, aryl, halo, haloalkyl, haloalkenyl, haloalkynyl, haloaryl, hydroxy, alkoxy, alkenyloxy, alkynyloxy, aryloxy, carboxy, benzyloxy, haloalkoxy, haloalkenyloxy, haloalkynyloxy, haloaryloxy, nitro, nitroalkyl, nitroalkenyl, nitroalkynyl, nitroaryl, nitroheterocyclyl, azido, amino, alkylamino, alkenylamino, alkynylamino, arylamino, benzylamino, acyl, alkenylacyl, alkynylacyl, arylacyl, acylamino, acyloxy, aldehydo, alkylsulphonyl, aryisulphonyl, alkylsulphonylamino, arylsulphonylamino, alkylsulphonyloxy, arylsulphonyloxy, heterocyclyl, heterocycloxy, helerocyclylamino, haloheterocyclyl, alkylsulphenyl, arylsulphenyl, carboalkoxy, carboaryloxy, mercapto, alkylthio, arylthio, acylthio and the like.

The polysiloxane macrodiols may be obtained as commercially available products such as X-22-160AS from Shin Etsu or prepared according to known procedures[8]. The preferred molecular weight range of the polysiloxane macrodiol is about 200 to about 6000, more preferably about 400 to about 1500. Polyurethane elastomeric compositions having polysiloxane macrodiols falling within this preferred molecular weight range offer particularly improved clarity and mechanical properties.

Suitable polyether macrodiols include those represented by the formula (II)

$$\text{HO—[(CH}_2)_m\text{—O]}_n\text{—H} \qquad (II)$$

wherein m is an integer of 4 or more, preferably 5 to 18; and n is an integer of 2 to 50.

Polyether macrodiols of formula (II) wherein m is 5 or higher such as polyhexamethylene oxide (PHMO), polyheptamethylene diol, polyoctamethylene oxide (POMO) and polydecamethylene oxide (PDMO) are preferred over the conventional PTMO. These polyethers, due to their hydrophobic nature, are more miscible with PDMS macrodiols and yield polyurethanes that are compositionally homogeneous, have high molecular weights and display improved clarity.

In a particularly preferred embodiment, the polyurethane elastomeric composition includes a soft segment derived from a polysiloxane macrodiol and a polyether macrodiol of formula (II) defined above.

The polyether macrodiols may be prepared by the procedure described by Gunatillake et al[9]. Polyethers such as PHMO described in this reference are more hydrophobic than PTMO and are more compatible with polysiloxane macrodiols. The preferred molecular weight range of the polyether macrodiol is about 200 to about 5000, more preferably about 200 to about 1200.

Suitable polycarbonate macrodiols include poly(alkylene carbonates) such as poly(hexamethylene carbonate) and poly(decamethylene carbonate); polycarbonates prepared by reacting alkylene carbonate with alkanediols for example 1,4-butanediol, 1,10-decandiol (DD), 1,6-hexanediol (HD) and/or 2,2-diethyl 1,3-propanediol (DEPD); and silicon based polycarbonates prepared by reacting alkylene carbonate with 1,3-bis (4-hydroxybutyl)-1,1,3,3-tetramethyldisiloxane (BHTD) and/or alkanediols.

It will be appreciated when both the polyether and polycarbonate macrodiols are present, they may be in the form of a mixture or a copolymer. An example of a suitable copolymer is a copoly(ether carbonate) macrodiol represented by the formula (III)

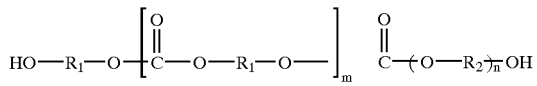

(III)

wherein $R_1$ and $R_2$ are same or different and selected from an optionally substituted straight chain, branched or cyclic, saturated or unsaturated hydrocarbon radical; and m and n are integers of 1 to 20.

Although the compound of formula (III) above indicates blocks of carbonate and ether groups, it will be understood that they also could be distributed randomly in the main structure.

The polyurethane elastomeric compositions of the present invention may be prepared by any suitable known technique. A preferred method involves mixing the polysiloxane macrodiol, polyether and/or polycarbonate macrodiol and chain extender and then reacting this mixture with a diisocyanate. The initial ingredients are preferably mixed at a temperature in the range of about 45 to about 100° C., more preferably about 60 to about 80° C. If desired, a catalyst such as dibutyl tin dilaurate at a level of about 0.001 to about 0.5 wt % based on the total ingredients may be added to the initial mixture. The mixing may occur in conventional apparatus or within the confines of a reactive extruder or continuous reactive injection molding machine.

Alternatively, the polyurethanes may be prepared by the prepolymer method which involves reacting a diisocyanate with the polysiloxane and polyether and/or polycarbonate macrodiols to form a prepolymer having terminally reactive diisocyanate groups. The prepolymer is then reacted with a chain extender.

Thus, the polyurethane elastomeric composition of the present invention may be further defined as including a reaction product of:

(i) macrodiols including:
(a) polysiloxane macrodiol; and
(b) a polyether and/or polycarbonate macrodiol;

(ii) a diisocyanate; and (iii) a chain extender.

Preferably, the diisocyanate is selected from 4,4'-methylenediphenyl diisocyanate (MDI), methylene bis (cyclohexyl) diisocyanate (H12MDI), p-phenylene diisocyanate (p-PDI), trans-cyclohexane-1,4-diisocyanate (CHDI) or a mixture of the cis and trans isomers, 1,6-hexamethylene diisocyanate (DICH), 2,4-toluene diisocyanate (2,4-TDI) or its isomers or mixtures thereof, p-tetramethylxylene diisocyanate (p-TMXDI) and m-tetramethylxylene diisocyanate (m-TMXDI). MDI is particularly preferred.

The chain extender is preferably selected from 1,4-butanediol, 1,6-hexanediol, 1,8-octanediol, 1,9-nonadiol, 1,10-decanediol 1,4-cyclohexane dimethanol, p-xyleneglycol, 1,4-bis (2-hydroxyethoxy) benzene and 1,12-dodecanediol. 1,4-butanediol is particularly preferred.

The methods described above here do not generally cause premature phase separation and yield polymers that are compositionally homogeneous and transparent having high molecular weights. These methods also have the advantage of not requiring the use any solvent to ensure that the soft and hard segments are compatible during synthesis.

A further advantage of the incorporation of the polysiloxane segment according to the present invention is the relative ease of processing of the polyurethane by conventional methods such as extrusion, injection and compression moulding without the need of added processing waxes. If desired, however, conventional polyurethane processing additives such as catalysts for example dibutyl tin dilaurate (DBTD), stannousoxide (SO), 1,8-diazabicyclo[5,4,0]undec-7-ene (DABU), 1,3-diacetoxy-1,1,3,3,-tetrabutyldistannoxane (DTDS), 1,4-diaza-(2,2,2)-bicyclooctane (DABCO), N,N,N',N'-tetramethylbutanediamine (TMBD) and dimethyllin dilaurate (DMTD); antioxidants for example Inganox (Registered Trade Mark); radical inhibitors for example trisnonylphenyl phosphite (TNPP); stabilisers; lubricants for example Irgawax (Registered Trade Mark); dyes; pigments; inorganic and/or organic fillers; and reinforcing materials can be incorporated into the polyurethane during preparation. Such additives are preferably added to the macrodiol mixture.

The polysiloxane macrodiol, polyether macrodiol, diisocyanate and the chain extender may be present in certain preferred proportions. The preferred level of diisocyanate and chain extender in the composition is about 30 to about 60 wt %, more preferably about 30 to about 50 wt %, most preferably about 40 wt %. The weight ratio of polysiloxane to polyether and/or polycarbonate may be in the range of from 1:99 to 99:1. A particularly preferred ratio of polysiloxane to polyether and/or polycarbonate which provides increased degradation resistance and stability is 80:20.

A particularly preferred polyurethane elastomeric composition includes a soft segment derived from 80 wt % of PDMS and 20 wt % of PHMO or PTMO and a hard segment derived from MDI and BDO.

The invention will now be described with reference to the following examples. These examples are not to be construed as limiting the invention in any way.

BRIEF DESCRIPTION OF THE DRAWINGS

In the examples, reference will be made to the accompanying drawings in which.

EXAMPLE 1

Figure 1:
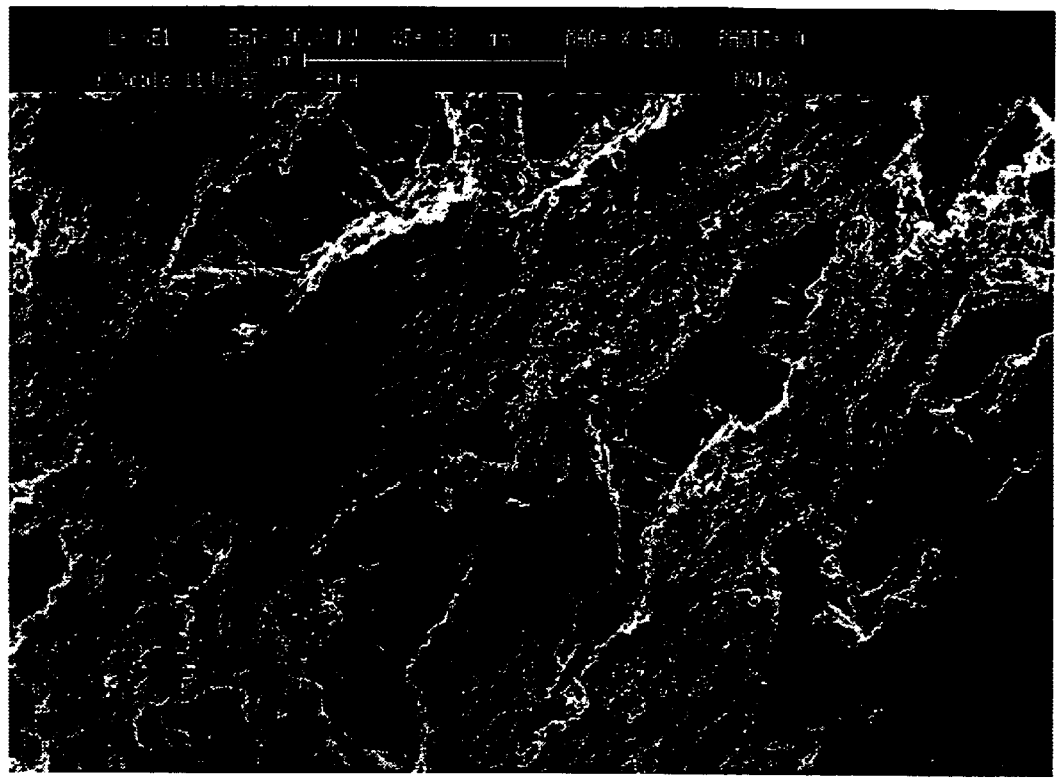
FIG. 1 is a photomicrograph of a commercial polyurethane Pellethane 2363-80A explanted after three months.
Figure 2:
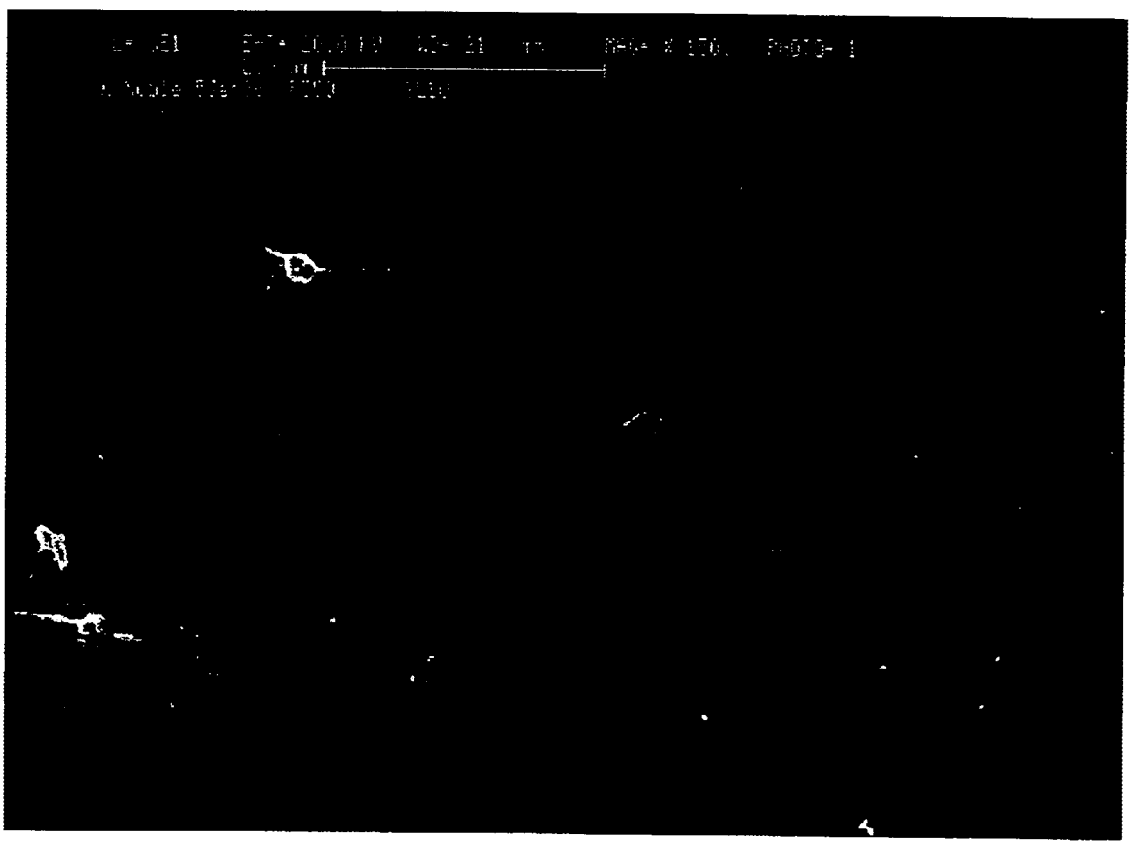
FIG. 2 is a photomicrograph of a commercial polyurethane Pellethane 2363-55D explanted after three months.
Figure 3:
FIG. 3 is a photomicrograph of a polyurethane composition based on PDMS/PHMO (80/20) explanted after three months.
Figure 4:
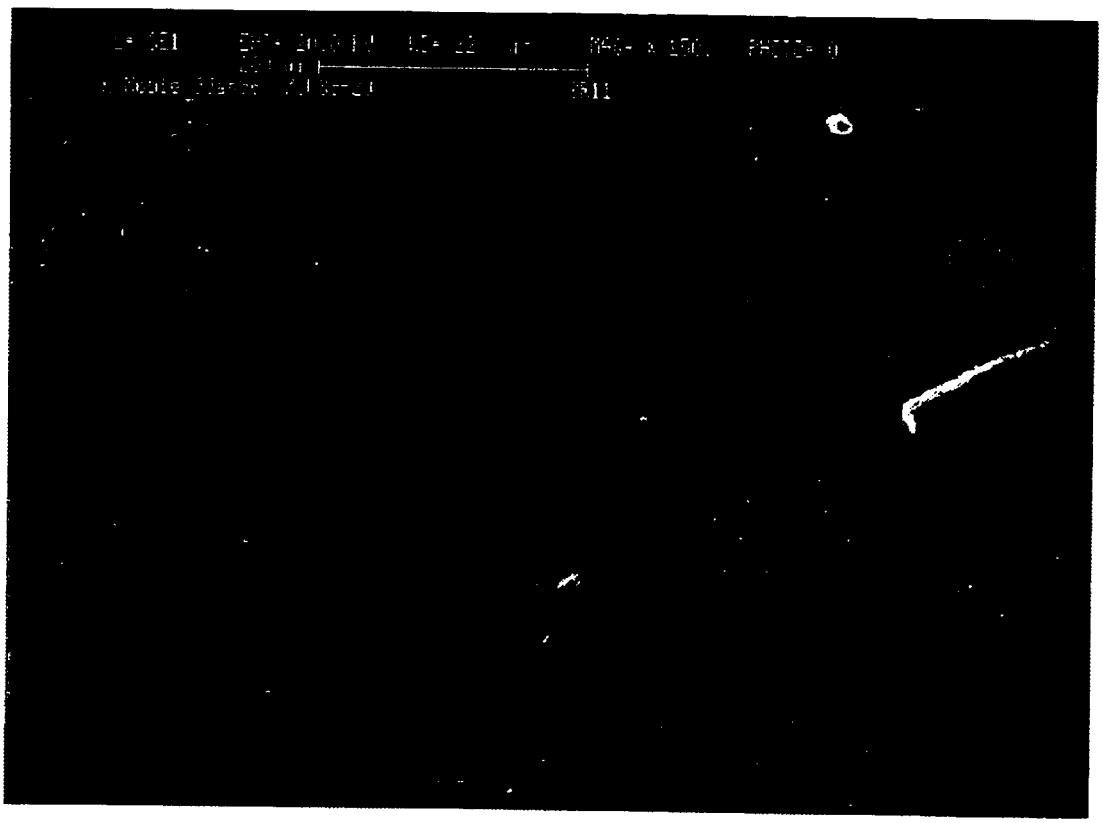
FIG. 4 is a photomicrograph of the polyurethane composition based on PDMS/PTMO (80/20) explanted after three months.
Figure 5:
FIG. 5 is a photomicrograph of the polyurethane composition based on PDMS/PHMO (20/80) explanted after three months.
Figure 6:
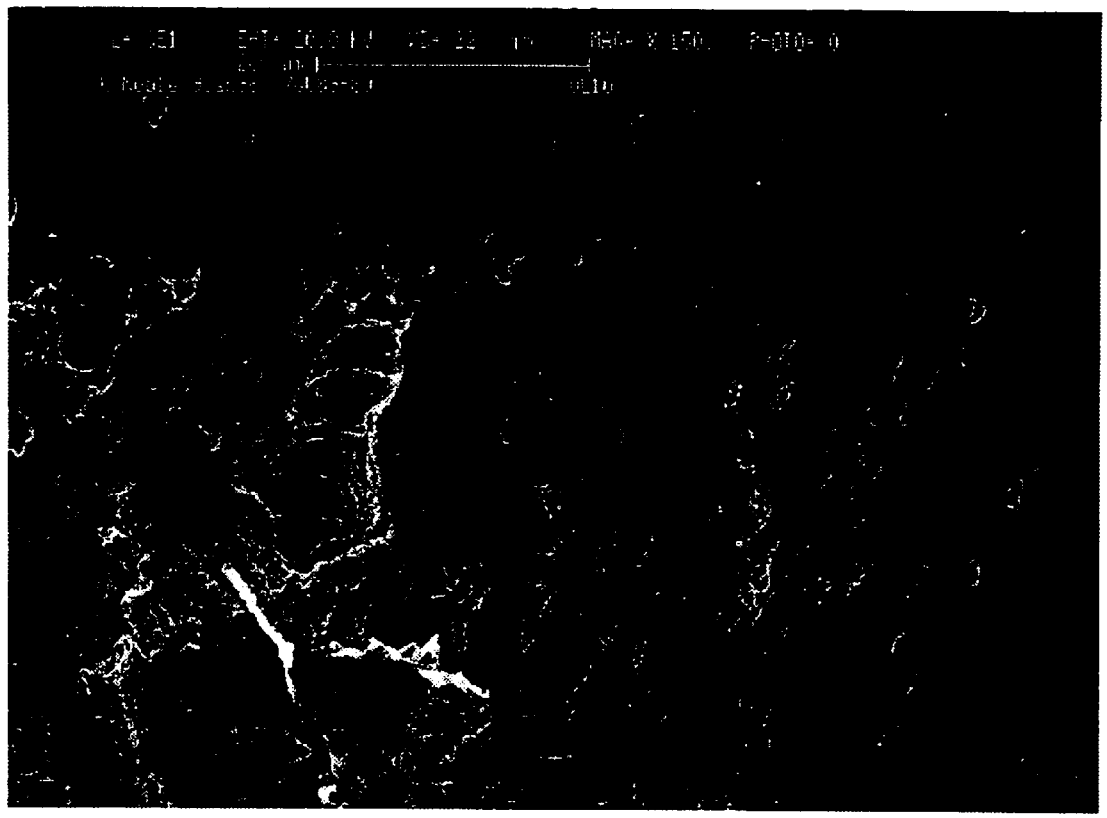
FIG. 6 is a photomicrograph of the polyurethane composition based on PDMS/PTMO (20/80) explanted after three months.

Two series of polyurethane compositions containing various proportions of PDMS/PHMO and PDMS/PTMO, respectively, were prepared by a one-step bulk polymerisation procedure. α,ω-Bis(hydroxyethoxypropyl) polydimethylsiloxane (Shin Etsu product X-22-160AS, MW 947.12) (PDMS), containing 0.1 wt % of tris(nonylphenyl) phosphite (TNPP) was dried at 105° C. for 15 h under vacuum (0.1 torr). Poly(hexamethylene oxide) (PHMO), prepared according to a method described in Gunatillake et al[9] and U.S. Pat. No. 5,403,912, was dried at 130° C. with 0.1 wt % TNPP (based on PHMO weight) under vacuum (0.1 torr) for 4 h. The molecular weight of the PHMO was 851.54. Poly(tetramethylene oxide) (PTMO, Terathane 1000 (Registered Trade Mark) from DuPont) was dried at 105° C. with 0.1 wt % TNPP (based on PTMO weight) under vacuum (0.1 torr) for 15 h.

The following preparation of a PDMS/PHMO polyurethane is an example of a general procedure for the one-step bulk polymerisation. Other PDMS/PHMO ratios and the PDMS/PTMO polyurethanes were prepared similarly.

A mixture of dried PDMS (120.0 g), PHMO (30.00 g) and 1,4-butanediol (15.94 g) was placed into a 500 ml polypropylene beaker and degassed by placing the beaker in an oven at 80° C. for 1.5 h under vacuum (2 torr). Molten MDI (84.06 g) at 60° C. was weighed in a fume hood into a 100 ml polypropylene beaker. The polyol mixture was allowed to cool to 70° C. under nitrogen after adding the catalyst, dibutyltin dilaurate (0.0125 g). The MDI was then quickly added with rapid stirring using a stainless steel spatula. The mixture, which was initially cloudy, turned clear with mixing after about 10 sec. The viscous mixture was rapidly poured onto a teflon coated metal tray and cured in an oven under nitrogen at 100° C. Heating was discontinued after 4 h and the sheet of polyurethane was allowed to cool to ambient temperature over a period of about 15 h.

The two series of polyurethanes prepared as described above contained 0, 20, 40, 60, 80 and 100 wt % of PDMS in the macrodiol mixture.

The thermal processability of each of the polyurethane compositions was evaluated by extrusion into thin films (0.2 mm thick) using a single screw Brabender extruder. All polyurethanes were dried under nitrogen at 85° C. overnight prior to the extrusion. The extrudability of the polyurethanes was assessed by observing the clarity of the film, melt strength, post extrusion tackiness, appearance (presence of "gels" or other particulate matter), and sensitivity to variation in processing temperature.

In the PHMO series, the composition made from a macrodiol mixture containing 80% PDMS and 20% PHMO showed optimal processability. The 100% PDMS composition, also extruded well but showed high level of "gel" like particles in the film and the surface was rough to feel. It also had inferior mechanical properties as discussed hereinafter. Films made from polyurethanes containing macrodiol mixtures containing 20, 40 and 60% PDMS, had inferior clarity to those prepared from the 80% PDMS composition.

The extrudability of the PDMS/PTMO series was generally poor compared to the PHMO series. In particular, those compositions with low PDMS content (20 and 40%) exhibited poor melt strength and the films were not transparent. The composition prepared from a macrodiol containing 80% PDMS produced films with good clarity and overall was the best in the PTMO series. The 80% PDMS/20% PHMO analogue was, however, superior in its processability.

The degradation resistance of the two series (PDMS/PHMO and PDMS/PTMO) of polyurethane compositions with 100, 80, 50 and 20 wt % PDMS was examined by a three month ovine implant experiment.

Each polyurethane composition, along with Pellethane (Registered Trade Mark) 2363-80A and 2363-55D was compression moulded into sheets of 0.5 mm thickness. Specimens shaped as dumbbells were cut from the sheets and stretched over poly(methyl methacrylate) holders. This caused the central section to be strained to 250% of its original length. A polypropylene suture was firmly tied around the centre of each specimen. This caused a localised increase in stress in the specimen. This test method provides a means of assessing the resistance to biodegradation by environmental stress cracking.

The specimens attached to their holders were sterilised with ethylene oxide and implanted into the subcutaneous adipose tissue in the dorsal thoraco-lumbar region of adult crossbred wether sheep.

After a period of three months the polyurethanes were retrieved. Attached tissue was carefully dissected away and the specimens were washed by soaking in 0.1 M sodium hydroxide for 2 days at ambient temperature followed by rinsing in deionised water. The specimens were then dried in air and examined by scanning electron microscopy (SEM) for signs of pitting or cracking. Compositions in which the macrodiol was 80% or 100% PDMS showed the best resistance to degradation. Representative scanning electron photomicrographs of two compositions and two commercial polyurethanes are shown in FIGS. 1 to 6.

The mechanical properties of the polyurethanes prepared in this example were also examined.

Figure 7:
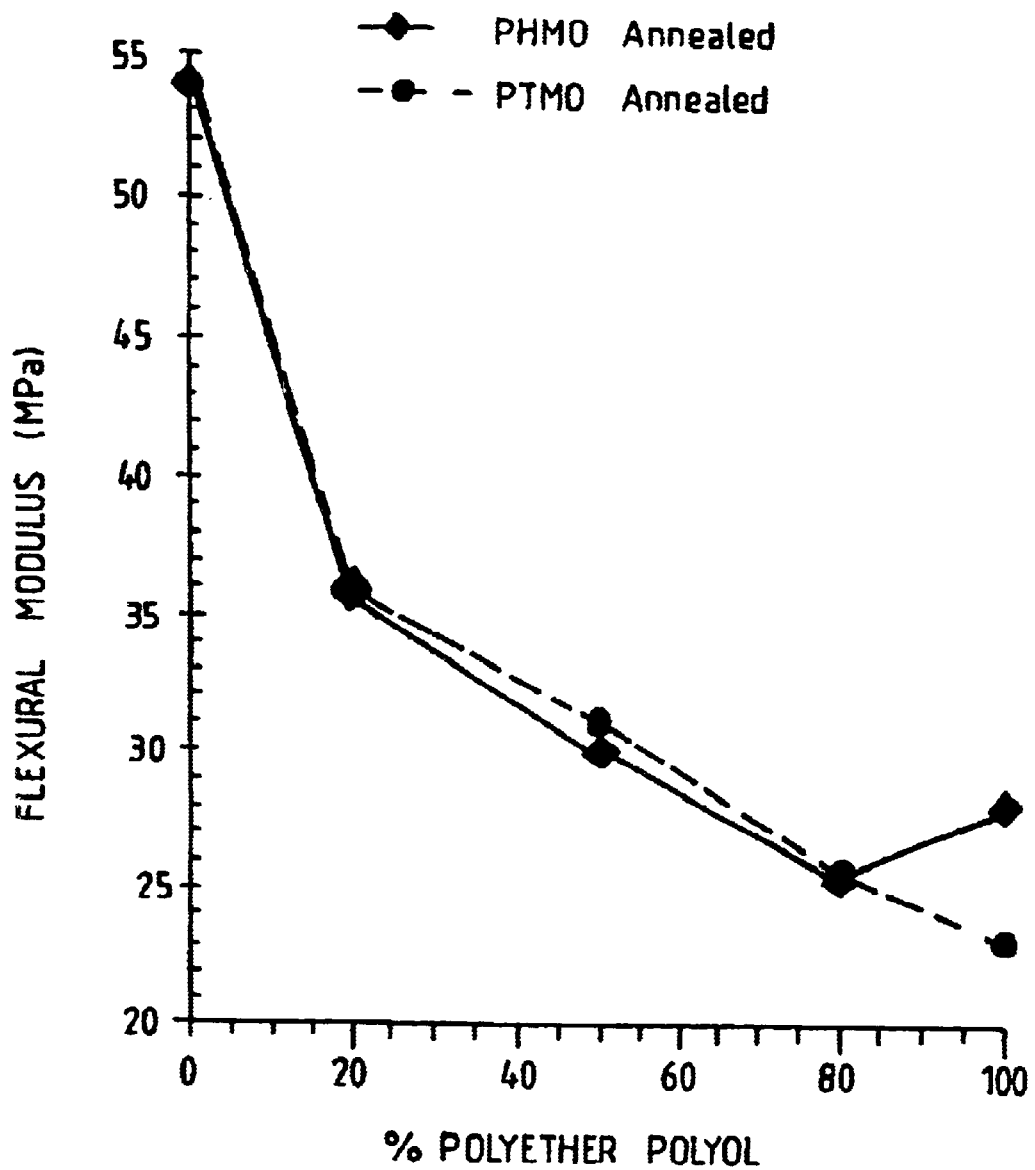
FIG. 7 is a graph showing flexural modulus of various PDMS, PHMO and PDMS/PTMO based polyurethane compositions.
Figure 8:
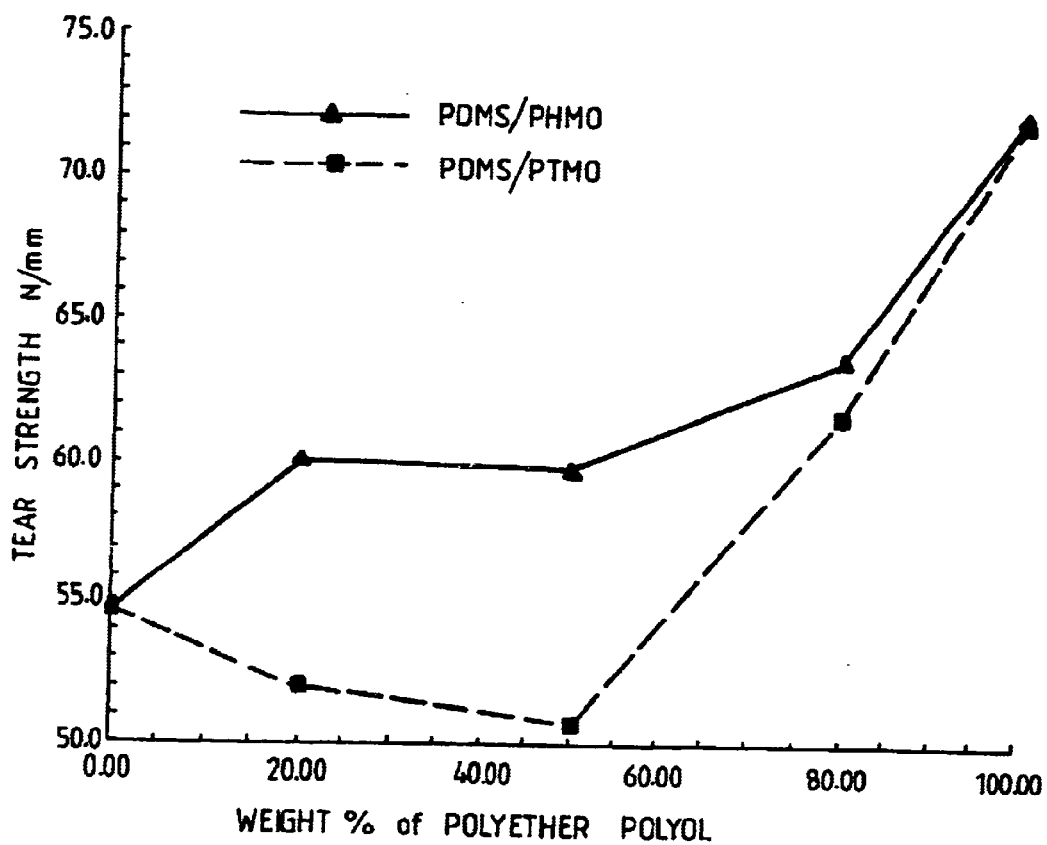
FIG. 8 is a graph showing tear strength of various PDMS/PHMO and PDMS/PTMO based polyurethane compositions.

FIGS. 7 and 8 show the variation of flexural modulus and tear strength of polyurethanes prepared from PDMS/polyether macrodiol mixtures.

Table 1 below lists the tensile and other properties of the polymer prepared from PDMS/PHMO mixture (80:20), along with those for two commercial medical-grade polyurethanes, Pellethane (Registered Trade Mark) 2363-80A and 2363-55D.

This data shows that a particularly suitable combination of biostability (degradation resistance), processability and mechanical properties is achieved with PDMS/PHMO in a ratio of about 80/20 for medical implant materials.

TABLE 1

| Property | Polyurethane based on PDMS/PHMO (80/20) | Pellethane 2363-80A† | Pellethane 2363-55D† |
| --- | --- | --- | --- |
| Shore Hardness | 84A | 82A | 55D |
| Ultimate Tensile‡ (MPa) | 25.5 ± 1 | 33.7 ± 1.8 (31) | 40.3 ± 1.8 (48) |
| Elongation at Break (%) | 460 ± 18 | 430 ± 20 (550) | 328 ± 16 (390) |
| Young's Modulus (MPa) | 22.5 ± 2 | 13 ± 2 (NA) | 87 ± 10 (NA) |
| Stress at 100% Strain (MPa) | 8.3 ± 5 | 8 (6) | 20 (17) |
| Stress at 200% Strain (MPa) | 12 ± 1 | 11 (NA) | 29 (NA) |
| Stress at 300% Strain (MPa) | 17 ± 1 | 18 (12) | 37 (35) |

TABLE 1-continued

| Property | Polyurethane based on PDMS/PHMO (80/20) | Pellethane 2363-80A† | Pellethane 2363-55D† |
|---|---|---|---|
| Tear Strength ¶ (N · mm$^{-1}$) | 60 ± 2 | 72 (83) | (115) |
| Abrasion Resistance § (mg per 1000 cycles) | 40 | 10 (20) | (80) |

†Manufacturer's values in parentheses
‡ASTM D 412
¶ASTM D 624 (Die C)
§ASTM D 1044 (Taber Abrader with 1000 gm and H22 wheel)

EXAMPLE 2

Two series of PDMS/PHMO and PDMS/PTMO based polyurethane compositions were also prepared according to a two-step bulk polymerisation procedure. PDMS (Shin Etsu product X-22-160AS, MW 947.12), PHMO and PTMO were dried prior to the experiment using the conditions described in Example 1. The following procedure, used to prepare a polyurethane composition containing PDMS/PHMO (80/20 w/w), illustrates the polymerisation employed to prepare the two series of polyurethanes of this Example.

MDI (28.30 g) and dibutyltin dialurate (0.004 g) were placed in a 250 mL reaction flask fitted with an addition funnel, condenser and nitrogen inlet, and heated at 80° C. to melt the MDI. PDMS (40.00 g) was added via the addition funnel to the MDI with stirring over a period of 10 min. After 30 min of reaction at 80° C., PHMO (10.00 g) was added to the mixture and the reaction was continued for one hour. The resulting prepolymer was allowed to cool at 70° C. and 1,4-butanediol (5.031 g) was added using a syringe. The mixture was stirred for 15 seconds and then the polymer was poured onto a teflon-coated glass cloth and cured at 100° C. for 4 h. Using a similar procedure, five more polyurethanes were prepared having PDMS/PHMO (w/w) ratios of 100/0, 60/40, 20/80, 10/90 and 0/100. A similar series was prepared with PTMO and PDMS.

In both series, the composition with 80 wt % PDMS was the best in terms of the clarity of the as-synthesised material and of the thermally processed film. The ultimate tensile strength and elongation at break for the composition based on PDMS/PHMO (80/20) was 21 MPa and 330%, respectively, whereas those for PDMS/PTMO (80/20) were 19 and 310%, respectively. The composition based on 100% PDMS (no added polyether macrodiols) showed an ultimate tensile strength of only 14 MPa and the elongation at break was 330%.

EXAMPLE 3

PDMS (Shin Etsu product X-22-160AS, MW 947.12) and PHMO were dried as described in Example 1. PHMO (520.0 g, MW 856.8), PDMS (130.0 g, MW 970), 1,4-butanediol (75.52 g), Irgawax (2.800 g), Irganox-1010 (2.240 g) and dibutyltin dilaurate (0.0560 g, 0.005%) were placed in a 1L round bottom flask. The mixture was degassed at 80° C. for 2 h under vacuum (2.0 torr). The mixture (350 g) was weighed into a 1L polypropylene beaker and allowed to cool to 70° C. under nitrogen. MDI (189.32) melted at 60° C. was quickly added to the mixture which was then stirred for 10 seconds. The initially cloudy solution turned clear, and was quickly poured onto a teflon-coated stainless steel tray and cured at 100° C. for 4 h in an oven under nitrogen. The cured slab was clear and transparent and showed no visual evidence of any poorly dispersed additives, indicating that conventional additives could be incorporated into the composition. Two other compositions were similarly prepared containing 42 and 45 wt % of hard segment. Tensile properties and molecular weight data for the three compositions are shown in Table 2 below.

TABLE 2

| Composition No. | % Hard segment | Mn (Mw/Mn) | UTS (MPa) | Fail strain (%) | Stress at 100% elongation (MPa) | Youngs Modulus |
|---|---|---|---|---|---|---|
| 1 | 40 | 107750 (2.08) | 25.5 | 460 | 8.3 | 22.3 |
| 2 | 42 | 102400 (1.87) | 27.2 | 420 | 9.2 | 26.4 |
| 3 | 45 | 99000 (1.91) | 25.2 | 415 | 11.7 | 38.9 |

EXAMPLE 4

MDI (28.65 g) was placed in a 250 ml reaction flask fitted with a condenser, nitrogen inlet and mechanical stirrer. A mixture of predried PDMS (Shin Etsu product X-22-160AS, MW 947.12) (PDMS) (10.00 g) and dibutyltin dilaurate (0.004 g) was added to the MDI and stirred at 80° C. for 30 min. Predried PDMO (40.00 gm, MW 822.64) was then added and the mixture was stirred for another 90 min. 1,4-Butanediol (4.683 g) was added to the mixture, stirring was continued for 15 seconds, and the polymer was quickly poured onto a tray covered with a teflon-coated glass cloth and cured for 4 h at 100° C. under nitrogen. The polymer molecular weight and polydispersity were 41250 and 2.52, respectively. The tensile properties were determined: fail stress 29.43 MPa, fail strain 435%, Stress at 100% elongation 13.6 MPa, tensile set 59% and Shore A hardness 85.

EXAMPLE 5

Four polyurethane compositions based on PDMS/PHMO (80/20) with and without the presence of conventional polyurethane additives were prepared using a two-step bulk polymerisation procedure. The macrodiol content was kept constant at 60 wt %, while two formulations with an isocyanate index of 1.00 and 1.03 were prepared for each additive free and additive containing composition. PDMS (Shin Etsu product X-22-160AS, MW 947.1) and PHMO (MW 696.1) were dried with 0.1 wt % TNPP as described in Example 1. For the additive free formulation, the two polyols were dried without TNPP.

Compositions with additives: PDMS (540.00 g), PHMO (135.00 g), Irgawax (2.80 g) and Irganox 1010 (2.240 g) were placed in a 2 L flask and degassed for 2 h at 80° C. under vacuum (0.1 torr). MDI (367.62 g) was placed in a 3 L three-necked round bottom flask fitted with a mechanical stirrer, nitrogen inlet and an addition funnel. The flask was then placed in an oil bath at 70° C. The degassed polyol mixture (652.71 g) was added from the addition funnel to MDI while stirring the mixture over a period of about 30 min. After completing the addition the mixture was stirred at 80° C. for 90 min to complete the reaction. The prepolymer was then degassed under vacuum (0.1 torr) at 80° C. for 30 min, and 490.0 g each of prepolymer was weighed into two 1L polypropylene beakers. Two polyurethane compositions with isocyanate index of 1.00 and 1.03, respectively were prepared by adding 1,4-butanediol (31.55 and 29.71 g, respectively) to the prepolymer (490.00 g). The polyurethanes were cured at 100° C. for 4 h in an oven under nitrogen.

Compositions without additives: Two polyurethane compositions with isocyanate index of 1.00 and 1.03, respectively were prepared by the same procedure used above, except additives TNPP, Irgawax and Inganox were not used in the formulation.

The four polyurethane compositions prepared in this example were extruded into 0.5 mm thick ribbons using a single screw Brabender extruder. All four materials extruded to give clear and homogeneous ribbons, despite the absence of conventional processing additives. Unlike conventional polyurethanes, all extruded materials had minimal post extrusion tackiness which enabled the tapes to be handled easily. The tensile properties of the materials tested as dumbbells punched from the extruded tape as well as from compression moulded sheets are shown in Table 3. As seen from the results, there was no significant difference in properties indicating the absence of degradation during extrusion notwithstanding the absence of conventional antioxidants and processing waxes.

thick sheet and tested for tensile properties using an Instron Tensile Testing Machine. The polymer showed 24 MPa ultimate tensile strength, 385% elongation at break, 33 MPa Young's modulus, 10 MPa stress at 100% elongation, 64 N/mm Tear strength, 25 MPa flexural modulus and a Shore hardness of 80A.

EXAMPLE 7

Two additive free polyurethane compositions based on mixtures of PDMS (MW 937.8) and PTMO (MW 998.2) macrodiols were prepared by a two step bulk polymerisation procedure to demonstrate the superior processing characteristics of compositions with high PDMS content. The two compositions were based on 80 and 20 wt %, respectively of PDMS in PTMO.

The two polyols were dried as described in Example 1 except that no TNPP was used. PDMS (400.0 g, MW 937.8) and PTMO (100 g, MW 998.2) were placed in a 2L flask and degassed for 2 h at 80° C. under vacuum (0.1 torr). Molten MDI (267.2 g) was placed in a 3L three-necked round bottom flask fitted with a mechanical stirrer, nitrogen inlet and an addition funnel. The flask was then placed in an oil bath at 70° C. The degassed polyol mixture (473.5 g) was

TABLE 3

| Composition | Isocyanate Index (N/CO/OH) | Fail Strain (%) | UTS (MPa) | Young's Modulus (MPa) | Stress at 100% Elongation (MPa) | Tensile Set (%) | Flexural Modulus (MPa) |
|---|---|---|---|---|---|---|---|
| Extruded Tape | | | | | | | |
| with additives | 1.00 | 390 | 20 | 36 | 10 | 43 | — |
| with additives | 1.03 | 365 | 21 | 37 | 11 | 26 | — |
| without additives | 1.00 | 410 | 20 | 39 | 11 | 38 | — |
| without additives | 1.03 | 415 | 24 | 38 | 12 | 28 | — |
| Compression Moulded Sheet | | | | | | | |
| with additives | 1.00 | 455 | 17 | 31 | 10 | 66 | 42 |
| with additives | 1.03 | 455 | 21 | 26 | 10 | 40 | 38 |
| without additives | 1.00 | 440 | 17 | 30 | 10 | 58 | 38 |
| without additives | 1.03 | 440 | 22 | 26 | 11 | 28.0 | 36 |

EXAMPLE 6

A polyurethane composition based on PDMS/PHMO (80/20), hydrogenated MDI (H$_{12}$MDI) and 1,4-butanediol was prepared using a one step bulk polymerisation procedure. The polyols were dried according to the procedure described in Example 1. H$_{12}$MDI (Aldrich) and BDO (Aldrich) were used.

PDMS (40.00 g), PHMO (10.00 g), BDO (5,595 g) and dibutylin dilaurate (0.008 g) were weighed into a 200 mL polypropylene beaker and degassed under vacuum (2 torr) at 80° C. for 2 h. Molten H$_{12}$MDI (30.612 g) was weighed into a wet tared-polypropylene beaker and added to the degassed polyol mixture and stirred for 45 sec. The resulting clear and transparent viscous polymer was cured at 100° C. for 12 h in an oven under nitrogen. The cured polymer, a clear and transparent rubbery material, showed a number average molecular weight of 62460 and a polydispersity of 1.88. The polymer was compression moulded at 180° C. to a 1 mm added from the addition funnel to MDI while stirring the mixture over a period of about 30 min. After completing the addition, the mixture was heated at 80° C. for 90 min with stirring under nitrogen. The prepolymer after degassing under vacuum (0.1 torr) was weighed (715.00 g) into a 2L polypropylene beaker. 1,4-Butanediol (46.79 g) was quickly added to the prepolymer and stirred thoroughly for 1 min and poured onto a teflon coated metal pan where it was cured at 100° C. for 4 h in an oven under nitrogen.

The second polyurethane composition was prepared using a similar procedure except that PTMO (400.0 g), PDMS (100.0 g), MDI (280.86 g) and 1,4-butanediol (52.472 g) were used. The two polyurethanes were extruded into tapes of about 0.8 mm thickness using a single screw Brabender extruder. The tape extruded from the polyurethane composition with 20% PDMS in the macrodiol mixture was opaque whereas the composition with 80% PDMS produced a very clear and transparent tape. Increasing the draw ratio to produce a thin tape or variation of processing temperatures did not produce tapes with any significant improvement in clarity in the former case. In both cases, the optimum processing temperatures were 150, 175, 203 and 205° C., respectively for zone 1, zone 2, zone 3 and die.

The clarity of the extruded films was assessed using a Gardner Hazemeter (Model No. UX10) and the results along with those for clear glass and Parafilm for comparison are summarised in Table 4. These results clearly demonstrated that the polyurethane composition based on PTMO/PDMS (20/80), a more preferred composition in the present invention, produced films with clarity comparable to that of glass. On the other hand the film obtained from PU based on PTMO/PDMS (80/20) was not clear.

TABLE 4

| Sample | Hazemeter Reading |
| --- | --- |
| Polyurethane from PTMO/PDMS (80/20) | 51 |
| Polyurethane from PTMOS/PDMS (20/80) | 2.0 |
| Clear glass (microscope slide) | 1.5 |
| Parafilm | 50 |

EXAMPLE 8

Two polyurethane compositions were prepared using each of low molecular weight PHMO (MW 529.0) and PTMO (MW 660.4) with PDMS (MW 937.8) in a 50150 (w/w) composition, respectively. The polyurethanes were prepared without any additives or catalyst.

Macrodiols were dried using the procedure described in Example 1 and the two polyurethanes were prepared by a two step bulk polymerisation procedure similar to that described in Example 7. The PHMO/PDMS polyurethane was prepared first by reacting PDMS (200.00 g) and PHMO (200.00 g) with MDI (237.07 g) to form the prepolymer at 80° C. The resulting prepolymer (574.70 g) was then mixed with BDO (26.69) and cured at 100° C. for 4 h under nitrogen. Similarly, the PTMO/PDMS polyurethane was prepared by reacting PDMS (200.00 g), PTMO (200.00 g), MDI (232.05) and BDO (34.62 g).

The two polyurethanes were extruded into tapes of about 0.8 mm thickness using a single screw Brabender extruder. The tape extruded from the polyurethane composition with PTMO in the macrodiol mixture was opaque whereas the PHMO-based material produced a very clear and transparent tape. Increasing the draw ratio to produce a thin tape or variation of processing temperatures did not produce tapes with any significant improvement in clarity in the former case. In both cases the optimum extruder processing temperatures were 150, 175, 203 and 205° C., respectively for zone 1, zone 2, zone 3 and die.

The clarity of the extruder films was assessed using a Gardner Hazemeter (Model No. UX10) and the results along with those for clear glass and Parafilm for comparison are summarised in Table 5. The results demonstrated that the PHMO-based polyurethane is significantly more clearer than the PTMO-based polyurethane.

TABLE 5

| Sample | Hazemeter Reading |
| --- | --- |
| PHMO/PDMS polyurethane | 3.3 |
| PTMO/PDMS polyurethane | 41 |

TABLE 5-continued

| Sample | Hazemeter Reading |
| --- | --- |
| Clear glass (microscope slide) | 1.5 |
| Parafilm | 50 |

EXAMPLE 9

Eight polyurethanes were prepared using a range of common catalysts used in the art to test their catalytic effect in a one step bulk polymerisation procedure.

The catalysts investigated included stannous octoate (SO), dibutyltin dilaurate (DBTD), 1,8-diazabicyclo[5,4,0]undec-7-ene (DABU), 1,3-diacetoxy-1,1,3,3,-tetrabutyldistannoxane (DTDS), 1,4-diaza-(2,2,2)-bicyclooctane (DABCO), N,N,N',N'-tetra- methylbutanediamine (TMBD) and dimethyltin dilaurate (DMTD).

PDMS (360.0 g, MW 940.3), PHMO (90.0 g, MW 696.1) and 1,4-butanediol (45.49 g) were degassed in a 1L round bottom flask for 1.5 h at 80° C. under vacuum (2 torr). Each catalyst (0.005 g, 0.008 wt % of total weight) was weighed into separate 200 mL polypropylene beakers with 40.0 g of the polyol mixture and placed in an oven at 70° C. under nitrogen. Molten MDI (20.55 g) at 70° C. was weighed into a wet tared beaker and added to the polyol mixture and stirred. The temperature increase in the reaction mixture was monitored by placing a thermocouple in the beaker connected to a chart recorder. The effectiveness of each catalyst was assessed by measuring the reaction gel time, rate of initial temperature rise and the polymer molecular weight, and clarity of the final product. The results are summarised in Table 6.

TABLE 6

| Sample No. | Catalyst | Reaction Temp after 12 sec (° C.) | Reaction Gel Time (sec) | Sample Clarity | Number Average Molecular Weight |
| --- | --- | --- | --- | --- | --- |
| 1 | control-no catalyst | 80 | 81 | opaque | 37670 |
| 2 | SO | 80 | 64 | opaque | 55520 |
| 3 | DBTD | 180 | 7 | transparent | 74850 |
| 4 | DABU | 80 | 34 | opaque | 59810 |
| 5 | DTDS | 160 | 6 | transparent | 90730 |
| 6 | DABCO | 85 | 43 | opaque | 37950 |
| 7 | TMBD | 80 | 63 | opaque | 39500 |
| 8 | DMTD | 172 | 6 | transparent | 84860 |

The results clearly demonstrate that the most effective catalysts for the preparation of transparent polyurethane compositions using a one step procedure are dibutyltindilaurate (DBTD), 1,3-diacetoxy-1,1,3,3,-tetrabutyldistannoxane (DTDS) and dimethyltindilaurate (DMTD).

EXAMPLE 10

Three polyurethane compositions were prepared by a one step catalysed polymerisation at initial mixing temperatures of 45, 60 and 80° C., respectively. PDMS (MW 969.7, 480.00 g), PHMO (MW 821, 120.00 g), BDO (63.42 g), Irgawax-280 (2.5 g), Irganox-1010 (2.0 g) and dibutyltin dilaurate (0.1 g) were placed in 1L round bottom flask and degassed at 80° C. under vacuum (2 torr) for 90 min. The degassed polyol mixture (658.50 g) was weighed in a 1L polypropylene beaker. After equilibrating the polyol mixture and MDI at 80° C., MDI (337.80 g) was quickly added to the polyol mixture and stirred. The polymer was poured onto a teflon coated metal pan and cured at 100° C. for 4 h in a nitrogen circulating oven. Similarly, two other compositions were prepared by equilibrating the polyol mixture and MDI to 45 and 60° C. respectively. The reaction mixtures in polymerisation at 60 and 80° C. turned to a clear solution during mixing, while that of the polymerisation at 45° C. stayed cloudy.

The reaction gel time, clarity of the polymer produced and the number average molecular weight of the cured polyurethanes are shown in Table 7.

TABLE 7

| Initial Reaction Temperature (° C.) | Appearance of the polyurethane as synthesised | Reaction Gel Time (sec) | Number Average Molecular Weight |
|---|---|---|---|
| 45 | opaque | 135 | 68550 |
| 60 | transparent | 30 | 104800 |
| 80 | transparent | 20 | 107600 |

EXAMPLE 11

In this example, uncatalysed one step polymerisation was carried out at several different initial mixing temperatures (50 to 110° C. temperature range) to demonstrate that specific reaction conditions are required to prepare polyurethanes that are compositionally homogeneous, clear and transparent with good mechanical properties.

PDMS (200.00 g), PHMO (50.00 g) and BDO (26.038 g) were mixed in a 500 mL flask and degassed at 80° C. under vacuum (2 torr) for 90 min. The polyol mixture (35.00 g) was weighed into each of five 100 mL polypropylene beakers and placed in an oven at 70° C. After equilibrating the polyol mixture and MDI to the desired initial reaction temperature, MDI (17.83 g) was quickly added and stirred. The reaction gel time and the clarity of the polymer formed were noted. The polymer was cured at 100° C. for 4 h in a nitrogen circulating oven. Initial reaction temperatures of 50, 70, 90 and 100° C. were examined. A control experiment was also carried out using dibutyltin dilaurate catalyst (at 0.005% level) at 70° C. initial reaction temperature, for comparison. The results are summarised in Table 8. With the exception of the polymer obtained in the catalysed polymerisation, all other polymers were brittle and low in molecular weight.

TABLE 8

| Initial Reaction Temperature (° C.) | Clarity of Polymer | Reaction Gel Time (sec) | Number Average Molecular Weight |
|---|---|---|---|
| 50 | opaque | 185 | 27200 |
| 70 | opaque | 102 | 41850 |
| 90 | opaque | 44 | 22182 |
| 110 | opaque | 39 | 35913 |
| 70 (with catalyst) | clear and transparent | 20 | 57400 |

EXAMPLE 12

Four polyurethane compositions with varying hard segment percentages were prepared using a one step polymerisation procedure similar to that described in Example 1. PDMS (Shin Etsu product X-22-160AS, MW 962.2) was dried at 105° C. under vacuum (0.1 torr) for 15 h while PHMO (MW 694.8) was dried at 135° C. under vacuum (0.1 torr) for 4 h.

A polyurethane with a hard segment composition of 45 wt % was prepared. PDMS (100.00 g), PHMO (25.00 g), dibutyltin dilaurate (0.011 g) and BDO (17.15 g) were degassed in a 500 mL polypropylene beaker by placing the beaker in an oven at 80° C. under a vacuum of 2 torr for 60 min. Molten MDI (85.12 g) at 60° C. was quickly added to the polyol mixture in the beaker while rapidly stirring with a stainless steel spatula. The mixture stayed cloudy during mixing and after about 1 min, the viscous polymer was poured onto a teflon coated tray and cured at 100° C. for 4 h in an oven under nitrogen. The cured polymer was opaque. Using a similar procedure, but with appropriate quantities, three other polyurethane compositions with hard segment percentages of 50, 55, and 60 wt % were prepared. In all cases the resulting polyurethanes were quite opaque and compositions with hard segment of 55 wt % and over were brittle. Table 9 shows the molecular weights of the polyurethanes prepared.

TABLE 9

| Wt % of Hard Segment | Number Average Molecular Weight | Polydispersity |
|---|---|---|
| 45 | 85865 | 1.69 |
| 50 | 57670 | 1.64 |
| 55 | 51460 | 1.65 |
| 60 | 56629 | 1.48 |

Of the four polyurethanes in this example only the composition with 45% hard segment was compression mouldable. The other three materials produced films that were very brittle and appeared to have very poor mechanical properties.

EXAMPLE 13

Four polyurethane compositions with varying hard segment levels were prepared using a two step bulk polymerisation procedure. PDMS (Shin Etsu product X-22-160AS, MW 962.2) and PHMO (MW 694.8) were dried as described in Example 12.

The following procedure illustrates the preparation of a composition with a hard segment weight percentage of 45. A mixture of PDMS (80.00 g) and PHMO (20.00 g) was degassed at 80° C. for 60 min under vacuum (0.1 torr). MDI (68.09 g) was placed in a three necked round bottom flask fitted with a mechanical stirrer, nitrogen inlet and an additional funnel. The polyol mixture (100.00 g) was added to MDI through the addition funnel over a period of 5 min at 70° C. under a slow stream of nitrogen. After the addition was complete, the reaction was continued for 2 h at 80° C. with stirring. The prepolymer was then degassed for 15 min at 80° C. under vacuum (0.1 torr). The prepolymer (160.00 g) was weighed into a 500 mL polypropylene beaker and chain extended with BDO (13.06 g). The polyurethane was then cured in a teflon coated metal pan at 100° C. in a nitrogen circulating oven for 4 h.

Using a similar procedure, three other compositions were prepared with hard segments at 50, 55, and 50 wt %. The molecular weights of the resulting polyurethanes are shown in Table 10. Table 11 shows the tensile properties of the resulting polyurethanes.

TABLE 10

| Wt % of Hard Segment | Number Average Molecular Weight | Polydispersity |
|---|---|---|
| 45 | 59810 | 1.41 |
| 50 | 52870 | 1.43 |
| 55 | 48000 | 1.41 |
| 60 | 47070 | 1.37 |

TABLE 11

| Hard Segment Wt % | Ultimate Tensile Strength (MPa) | Elongation at Break (%) | Young's Modulus (MPa) | Stress at 100% Elongation (MPa) | Shore Hardness |
|---|---|---|---|---|---|
| 45 | 15 | 285 | 58 | 12 | 41D |
| 50 | 24 | 300 | 131 | 18 | 50D |
| 55 | 22 | 175 | 193 | 22 | 57D |
| 60 | 30 | 200 | 220 | 27 | 65D |

The results in this example demonstrate that polyurethanes having hard segment levels as high as 60% and good mechanical properties could be prepared by using a two step polymerisation procedure.

EXAMPLE 14

Four polyurethane compositions were prepared by a one step bulk polymerisation procedure similar to that described in Example 12 except that PTMO (MW 1000) was used in place of PHMO. Similar to Example 12, the four compositions were formulated to have 45, 50, 55 and 60 wt % of hard segment. A polyurethane with a hard segment weight percentage of 45 was prepared as follows. PDMS (80.00 g), PHMO (20.00 g), dibutyltin dilaurate (0.01 g) and BDO (14.305 g) were degassed in a 500 mL polypropylene beaker by placing the beaker in an oven at 80° C. under a vacuum of 2 torr for 60 min. Molten MDI (67.513 g) at 60° C. was quickly added to the polyol mixture in the beaker while rapidly stirring with a stainless steel spatula. The mixture remained cloudy during mixing and after about 1 min, the viscous polymer was poured onto a teflon coated tray and cured at 100° C. for 4 h in nitrogen circulating oven. The cured polymer was opaque.

Using a similar procedure, but with appropriate quantities, three other polyurethane compositions with hard segment contents of 50, 55, and 60 wt % were prepared. In all cases the resulting polyurethanes were quite opaque and compositions with hard segment of 55 wt % and over were brittle. Table 12 shows the molecular weights of the polyurethanes prepared in this Example.

Similar to the results obtained in Example 12 with PHMO, the materials in this example were not compression mouldable to form plaques for tensile testing. The plaques formed were very brittle and broke during handling.

TABLE 12

| Wt % of Hard Segment | Number Average Molecular Weight | Polydispersity |
|---|---|---|
| 45 | 83950 | 1.6 |
| 50 | 63350 | 1.4 |
| 55 | 80150 | 1.5 |
| 60 | 73690 | 1.5 |

EXAMPLE 15

Two polyurethane compositions were prepared using PDMS (MW 2181), PHMO (MW 696.1) and PTMO (MW 660.4), respectively to investigate the effect of PDMS molecular weight on properties of polyurethanes. PDMS and PHMO were dried using conditions described in Example 12. PTMO was dried at 105° C. for 15 h under vacuum (0.1 torr). The hard segment weight percentage was kept constant at 40 wt % for both materials.

PDMS (20.00 g), PHMO (5.00 g), dibutyltin dilaurate (0.002 g) and BDO (3.226 g) were degassed in a 100 mL polypropylene beaker by placing the beaker in an oven at 80° C. under a vacuum of 2 torr for 60 min. Molten MDI (13.44 g) at 60° C. was quickly added to the polyol mixture in the beaker while rapidly stirring with a stainless steel spatula. The mixture stayed cloudy during mixing and after about 1 min, the viscous polymer was poured onto a teflon coated tray and cured at 100° C. for 4 h under nitrogen in an oven. The cured polymer was very opaque.

The second polyurethane was prepared using the same procedure, except that PDMS (20.00 g), PTMO (5.00 g), BDO (3.200 g), dibutyltin dilaurate (0.002 g) and MDI (13.467 g) were used. The cured polymer was very opaque as well. The number average molecular weights of the two polymers as determined by GPC were 97983 and 107940, respectively.

The two polymers were compression moulded at 210° C. to form 1 mm thick plaques, and tested for tensile properties using an Instron Tensile Machine. The polyurethane based on PHMO showed 3.8 MPa ultimate tensile strength, 70% elongation at break, 15 MPa Young's modulus, while the material based on PTMO showed 5.5 MPa ultimate tensile strength, 80% elongation at break, and 17 MPa Young's modulus. These results, therefore indicate that the PDMS molecular weight has a very significant influence on polyurethane properties.

The following Examples 16 to 21 illustrate the applicability of the present invention to prepare polyurethane compositions from mixtures of PDMS and polycarbonate macrodiols. Examples provided illustrate that for some combinations of macrodiols, the choice of the polymerisation method is crucial to prepare polyurethanes that are compositionally homogeneous and transparent with good mechanical properties. All polyurethanes in Examples 16 to 21 were formulated to have an isocyanate index of 1.03 and a 40 wt % hard segment based on MDI and BDO. PDMS (MW 937.8, Shin Etsu product X-22-160AS) was dried prior to polymerisation using the conditions described in Example 12. Tensile properties of the polyurethanes were measured using dumbbell shaped specimens, on an Instron Tensile Testing Machine.

EXAMPLE 16

In this example, two polyurethane compositions were prepared from a mixture of PDMS and poly(hexamethylene carbonate) macrodiols using, respectively one and two-step bulk polymerisation procedures. Poly(hexamethylene carbonate) (MW 893, Polysciences Inc.) was dried at 105° C. for 15 h under vacuum (0.1 torr).

In the one step polymerisation procedure, PDMS (40.00 g), poly(hexamethylene carbonate) (10.00 g), 1,4-butanediol (5.265 g) and dibutyltin dilaurate (0.008 g) were weighed into 200 mL polypropylene beaker and degassed at 80° C. under vacuum (2 torr) for 60 min. Molten MDI (28.07 g) was quickly added to the polyol mixture and stirred rapidly with a stainless steel spatula. During mixing, the solution stayed very cloudy and after about 15 sec, yielded an opaque solid material.

A mixture of PDMS (48.00 g) and poly(hexamethylene carbonate) (12.00 g) was degassed at 80° C. for 60 min under vacuum (0.1 torr). MDI (32.62 g) was placed in a 250 mL three necked round bottom flask fitted with a mechanical stirrer, nitrogen inlet and an addition funnel. The polyol mixture (60.00 g) was added to MDI through the addition funnel over a period of 15 min at 70° C., under a slow stream of nitrogen. After the addition was complete, the reaction was continued for 2 h at 80° C. with stirring. The prepolymer was then degassed for 15 min at 80° C. under vacuum (0.1 torr). The prepolymer (82.00 g) was weighed into a 250 mL polypropylene beaker and chain extended with BDO (5.53 g). The polyurethane was then cured in a teflon coated metal tray at 100° C. in a nitrogen circulating oven for 4 h.

Both polyurethanes were compression moulded into a 1 mm thick plaque. Dumbbells were punched from the plaques and tensile tested on an Instron Tensile Testing Machine. The polyurethane obtained by the one step polymerisation was very brittle and broke during handling, indicative of very poor mechanical properties, whereas the material obtained in the two step process showed 18 MPa ultimate tensile strength, 250% elongation at break, 57 MPa Young's modulus and 13 MPa stress at 100% elongation. These results demonstrate that the two step procedure was far superior to the one step method in preparing polyurethanes from the macrodiol mixture in this example.

EXAMPLE 17

This example illustrates the preparation of a polyurethane from PDMS and a polycarbonate macrodiol prepared from 1,10-decanediol (DD). The polycarbonate macrodiol was prepared from DD and ethylene carbonate according to a procedure described in U.S. Pat. No. 4,131,731.

A polyurethane composition was prepared by using a one step polymerisation procedure. The polycarbonate macrodiol (MW 729.79) was dried at 105° C. for 15 h under vacuum (0.1 torr). PDMS (40.00 g), polycarbonate macrodiol (10.00 g), 1,4-butanediol (4.872 g) and dibutyltin dilaurate (0.008 g) were weighed into a 250 mL polypropylene beaker and degassed at 80° C. under vacuum (2 torr) for 60 min. Molten MDI (28.46 g) was then added to the mixture in the beaker with rapid stirring with a stainless steel spatula for about 30 sec. The resulting viscous polyurethane was poured onto a teflon coated metal tray and cured at 100° C. in a nitrogen circulating oven for 4 h. The cured polymer was a clear and transparent rubbery material. The tensile properties of the polyurethane were 22 MPa ultimate tensile strength, 280% elongation at break, 53 MPa Young's modulus and 13 MPa stress at 100% elongation.

EXAMPLE 18

A polyurethane composition based on PDMS and a copolycarbonate macrodiol (MW 1088) prepared from 1,3-bis(4-hydroxybutyl)-1,1,3,3-tetramethyldisiloxane (BHTD) was synthesised. The copolycarbonate macrodiol was prepared from BHTD and ethylene carbonate according to a procedure described in U.S. Pat. No. 4,131,731. The polyurethane was prepared using a similar procedure to that described in Example 17, except that PDMS (10.00 g), polycarbonate macrodiol (2.50 g), 1,4-butanediol (1.293 g), MDI (7.040 g) and dibutyltin dilaurate (0.002 g) were used. The tensile properties of the polyurethane were 14 MPa ultimate tensile strength, 280% elongation at break, 37 MPa Young's modulus and 10 MPa stress at 100% elongation.

EXAMPLE 19

This Example illustrates the preparation of a polyurethane from PDMS and a polycarbonate macrodiol prepared from 1,10-decandediol (DD) and 1,6-hexanediol (HD). The polycarbonate macrodiol was prepared from a 50/50 (wt/wt) mixture of DD and HD, and ethylene carbonate according to a procedure described in U.S. Pat. No. 4,131,731.

A polyurethane composition was prepared by using a one step polymerisation procedure. The polycarbonate macrodiol (MW 623.6) was dried at 105° C. for 15 h under vacuum (0.1 torr). PDMS (40.00 g), polycarbonate macrodiol (10.00 g), 1,4-butanediol (4.716 g) and dibutyltin dilaurate (0.008 g) were weighed into a 250 mL polyproplene beaker and degassed at 80° C. under vacuum (2 torr) for 60 min. Molten MDI (28.617 g) was then added to the mixture in the beaker with rapid stirring with a stainless steel spatula for about 30 sec. The resulting viscous polyurethane was poured onto a teflon coated metal tray and cured at 100° C. in a nitrogen circulating oven for 4 h. The cured polymer was a clear and transparent rubber material. The tensile properties of the polyurethane were 22 MPa ultimate tensile strength, 300% elongation at break, 50 MPa Young's modulus and 12 MPa stress at 100% elongation.

EXAMPLE 20

A polyurethane composition using a mixture of PDMS and a copolycarbonate macrodiol (MW 1220) based on HD and 1,3-bis(4-hydroxybutyl)-1,1,3,3-tetramethyldisiloxane (BHTD) was prepared, using a one step bulk polymerisation procedure. The copolycarbonate was prepared from a 50/50 (wt/wt) mixture of the two diols and ethylene carbonate according to a procedure described in U.S. Pat. No. 4,131,731.

A polyurethane using PDMS (10.00 g), polycarbonate macrodiol (2.5 g), 1,4-butanediol (1.310 g), MDI (7.023 g) and dibutyltin dilaurate (0.002 g) was prepared using a procedure similar to that described in Example 19. The polyurethane which was clear and transparent, exhibited 18 MPa ultimate tensile strength, 280% elongation at break, 37 MPa Young's modulus and 11 MPa stress at 100% elongation.

EXAMPLE 21

A similar procedure to that described in Example 19 was used except that a copolycarbonate macrodiol (MW 1060) prepared from HD and 2,2'-diethyl 1,3-propanediol (DEPD) was used. The polyurethane composition was prepared by reacting PDMS (20.00 g), HD and DEPD-based copolycarbonate (5.00 g), BDO (2.578 g), dibutyltin dilaurate (0.002 g) and MDI (14.088 g). The polyurethane prepared showed 21 MPa ultimate tensile strength, 315% elongation at break, 70 MPa Young's modulus and 11 MPa stress at 100% elgonation.

REFERENCES

1. M. Szycher, J. Biomat. Appl., Vol 3, pp297–402 (1988).
2. L. Pinchuck, J. Biomater. Sci. Edn, Vol 3(3), pp225–267 (1994).
3. A. Braley, J. Macromol Sci., Chem., Vol A4, 529 (1970).
4. Jr. Ward, et al, Organometallic Polymers, Academic Press, New York (1978).
5. X. Yu, M. R. Nagarajan, T. G. Grasel, P. E. Gibson and S. L. Cooper. J. Polym. Sci. Polym. Phy., Vol 23, pp2319–2338 (1985).
6. T. A. Speckhard and S. L. Cooper, Rubber Chem. Technol. Vol 59, pp405–430 (1986).
7. R. A. Phillips, J. S. Stevenson, M. R. Nagarajan and S. L. Cooper, J. Macromol SciPhy., Vol B27(2&3) pp245–274 (1988).

8. P. M. Sormani, R. J. Minton, I. Yilgor, P. J. Andolino Brandt, J. S. Riffle, C. Tran and J. E. McGrath, *Polymer Preprints*, Vol 25(1) pp227–229 (1994).
9. P. A. Gunatillake, G. F. Meijs, R. C. Chatelier, D. M. McIntosh and E., Rizzardo *Polym. Int.* Vol.27, pp 275–283 (1992).

What is claimed is:

1. A polyurethane elastomeric composition comprising a hard segment and a soft segment, wherein the soft segment is formed from
   (a) a combination of at least one polyether macrodiol and at least one polycarbonate macrodiol, wherein the polyether macrodiol is a compound of the formula:

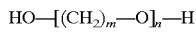

wherein
   m is an integer of 4 or more; and
   n is an integer from 2 to 50; and
   (b) at least one polysiloxane macrodiol of the formula (I):

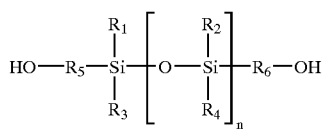

wherein
   $R_1$, $R_2$, $R_3$, $R_4$, $R_5$, and $R_6$ are each independently an optionally substituted straight chain, branched or cyclic, saturated or unsaturated hydrocarbon radical; and
   n is an integer from 1 to 100.

2. The polyurethane elastomeric composition of claim 1 wherein the hard segment is present in about 30 wt. % to about 60 wt. % of the polyurethane elastomeric composition and wherein the soft segment is present in about 40 wt. % to about 70 wt. % of the polyurethane elastomeric composition.

3. The polyurethane elastomeric composition of claim 1 wherein the soft segment is formed from about 10 wt. % to about 30 wt. % of a combination of at least one polyether macrodiol and at least one polycarbonate macrodiol.

4. The polyurethane elastomeric composition of claim 1 wherein the soft segment is formed from about 70 wt. % to about 90 wt. % of at least one polysiloxane macrodiol.

5. The polyurethane elastomeric composition of claim 1 wherein the soft segment is formed from (a) about 10 wt. % to about 30 wt. % of a combination of at least one polyether macrodiol and at least one polycarbonate macrodiol; and (b) from about 70 wt. % to about 90 wt. % of at least one polysiloxane macrodiol.

6. The polyurethane elastomeric composition of claim 1 wherein the hard segment is present in about 30 wt. % to about 50 wt. % of the polyurethane elastomeric composition.

7. The polyurethane elastomeric composition of claim 1 wherein the polysiloxane macrodiol is polydimethylsiloxane.

8. The polyurethane elastomeric composition of claim 1 wherein the molecular weight of the polysiloxane macrodiol is about 200 to about 6000.

9. The polyurethane elastomeric composition of claim 8 wherein the molecular weight of the polysiloxane macrodiol is about 400 to about 1500.

10. The polyurethane elastomeric composition of claim 1 wherein the polyether macrodiol is polytetramethylene oxide, polypentamethylene oxide, polyhexamethylene oxide, polyheptamethylene oxide, polyoctamethylene oxide, or polydecamethylene oxide.

11. The polyurethane elastomeric composition of claim 1 wherein the polycarbonate macrodiol is a poly(alkylene carbonate), a polycarbonate prepared by reacting an alkylene carbonate with an alkane diol, or a silicon-based polycarbonate.

12. The polyurethane elastomeric composition of claim 1 wherein the hard segment is the product of a diisocyanate and a chain extender.

13. The polyurethane elastomeric composition of claim 12 wherein the diisocyanate is 4,4'-methylenediphenyl diisocyanate; methylene bis diisocyanate; p-phenylene diisocyanate; cis-cyclohexane-1,4-diisocyanate; trans-cyclohexane-1,4-diisocyanate; a mixture of cis-cyclohexane-1,4-diisocyanate and trans-cyclohexane-1,4-diisocyanate; 1,6-hexamethylene diisocyanate; 2,4-toluene diisocyanate; cis-2,4-toluene diisocyanate; trans-2,4-toluene diisocyanate; a mixture of cis-2,4-toluene diisocyanate and trans-2,4-toluene diisocyanate; p-tetramethylxylene diisocyanate; or m-tetramethylxylene diisocyanate.

14. The polyurethane elastomeric composition of claim 12 wherein the chain extender is 1,4-butanediol; 1,6-hexanediol; 1,8-octanediol; 1,9-nonanediol; 1,10-decanediol; 1,12-dodecanediol; 1,4-cyclohexane dimethanol; p-xyleneglycol; or 1,4-bis(2-hydroxyethoxy) benzene.

15. The polyurethane elastomeric composition of claim 12 wherein the diisocyanate is 4,4'-methylenediphenyl diisocyanate and wherein the chain extender is 1,4-butanediol.

16. A device or article comprising an amount of a polyurethane elastomeric composition effective to render the device biocompatible, the polyurethane elastomeric composition comprising a hard segment and a soft segment, wherein the soft segment is formed from (a) a combination of at least one polyether macrodiol and at least one polycarbonate macrodiol; and (b) at least one polysiloxane macrodiol of formula (I):

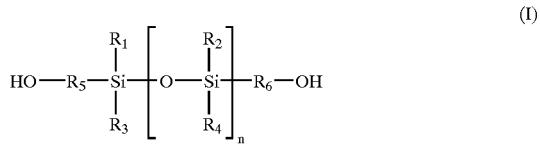

wherein
$R_1$, $R_2$, $R_3$, $R_4$, $R_5$, and $R_6$ are each independently an optionally substituted straight chain, branched or cyclic, saturated or unsaturated hydrocarbon radical; and
n is an integer from 1 to 100.

17. The device or article of claim 16 wherein the hard segment is present in about 30 wt. % to about 60 wt. % of the polyurethane elastomeric composition and wherein the soft segment is present in about 40 wt. % to about 70 wt. % of the polyurethane elastomeric composition.

18. The device or article of claim 16 which is a medical device, article or implant.

19. The device or article of claim 18 which is a cardiac pacemaker, defibrillator, catheter, implantable prosthesis, cardiac assist device, heart valve, vascular graft, extracorporeal device, artificial organ, pacemaker lead, defibrillator lead, blood pump, balloon pump, a-V shunt, biosensor, membrane for cell encapsulation, drug delivery device, wound dressing, artificial joint, orthopaedic implant or soft tissue replacement.

20. A device or article comprising a polyurethane elastomeric composition comprising a hard segment and a soft segment, wherein the soft segment is formed from
(a) a combination of at least one polyether macrodiol and at least one polycarbonate macrodiol, wherein the polyether macrodiol is a compound of the formula:

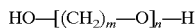

wherein
m is an integer of 4 or more; and
n is an integer from 2 to 50; and
(b) a polysiloxane macrodiol of formula (I):

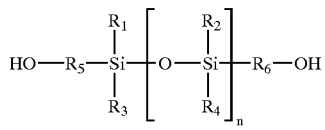

wherein
$R_1$, $R_2$, $R_3$, $R_4$, $R_5$, and $R_6$ are each independently an optionally substituted straight chain, branched or cyclic, saturated or unsaturated hydrocarbon radical; and
n is an integer from 1 to 100; and
wherein the device is artificial leather, a shoe sole, a cable sheathing, varnish, a coating, a structural component for a pump or vehicle, a mining ore screen, a conveyor belt, a laminating compound, a textile, a separation membrane, a sealant or an adhesive component.

21. A process for preparing a polyurethane elastomeric composition comprising:
a) mixing a polysiloxane macrodiol, a polyether macrodiol, a polycarbonate macrodiol, and a chain extender; and
b) reacting the mixture with a diisocyanate to yield a polyurethane elastomeric composition comprising a hard segment which is the product of a diisocyanate and a chain extender; and a soft segment which is the product of:
i) at least one polysiloxane macrodiol; and
ii) a combination of at least one polyether macrodiol and at least one polycarbonate macrodiol, wherein the polyether macrodiol is a compound of the formula:

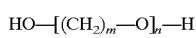

wherein
m is an integer of 4 or more; and
n is an integer from 2 to 50.

22. The process of claim 21, wherein the hard segment is about 30 wt. % to about 60 wt. % of the polyurethane elastomeric composition and wherein the soft segment is about 40 wt. % to about 70 wt. % of the polyurethane elastomeric composition.

23. The process of claim 21 wherein step (a) is performed at a temperature of about 45° C. to about 100° C.

24. The process of claim 21 wherein step (a) occurs in the presence of a catalyst.

25. The process of claim 24 wherein the catalyst is dibutyl tin dilaurate.

26. A process for preparing a polyurethane elastomeric composition comprising:

a) reacting a diisocyanate with a polysiloxane macrodiol, a polyether macrodiol, and a polycarbonate macrodiol, to form a prepolymer having terminally reactive diisocyanate groups; and
b) reacting the prepolymer with a chain extender to yield a polyurethane elastomeric composition comprising a soft segment which is the product of
(a) at least one polysiloxane macrodiol; and
(b) a combination of at least one polyether macrodiol and at least one polycarbonate macrodiol, wherein the polyether macrodiol is a compound of the formula:

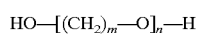

wherein
m is an integer of 4 or more;
n is an integer from 2 to 50; and
wherein the polyurethane elastomeric composition comprises a hard segment which is the product of a diiocyanate and a chain extruder.

27. The process of claim 26 wherein the hard segment is about 30 wt. % to about 60 wt. % of the polyurethane elastomeric composition and wherein the soft segment is about 40 wt. % to about 70 wt. % of the polyurethane elastomeric composition.

28. The process of claim 26 wherein the diisocyanate is 4,4'-methylenediphenyl diisocyanate; methylene bis diisocyanate; p-phenylene diisocyanate; cis-cyclohexane-1,4-diisocyanate; trans-cyclohexane-1,4-diisocyanate; a mixture of cis-cyclohexane-1,4-diisocyanate and trans-cyclohexane-1,4-diisocyanate; 1,6-hexamethylene diisocyanate; 2,4-toluene diisocyanate; cis-2,4-toluene diisocyanate; trans-2,4-toluene diisocyanate; a mixture of cis-2,4-toluene diisocyanate and trans-2,4-toluene diisocyanate; p-tetramethylxylene diisocyanate; or m-tetramethylxylene diisocyanate.

29. The process of claim 26 wherein the polysiloxane macrodiol is a compound of formula (I):

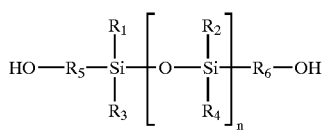

wherein
$R_1$, $R_2$, $R_3$, $R_4$, $R_5$, and $R_6$ are each independently an optionally substituted straight chain, branched or cyclic, saturated or unsaturated hydrocarbon radical; and
n is an integer from 1 to 100.

30. The process of claim 26 wherein the polyether macrodiol is polytetramethylene oxide, polypentamethylene oxide, polyhexamethylene oxide, polyheptamethylene oxide, polyoctamethylene oxide, or polydecamethylene oxide.

31. The process of claim 26 wherein the polycarbonate macrodiol is a poly(alkylene carbonate), a polycarbonate prepared by reacting an alkylene carbonate with an alkane diol, or a silicon-based polycarbonate.

32. The process of claim 19 wherein the chain extender is 1,4-butanediol; 1,6-hexanediol; 1,8-octanediol; 1,9-nonanediol; 1,10-decanediol; 1,12-dodecanediol; 1,4-cyclohexane dimethanol; p-xyleneglycol; or 1,4-bis(2-hydroxyethoxy) benzene.

33. A process for preparing a polyurethane elastomeric composition comprising a hard segment and a soft segment comprising:
a) forming a prepolymer having terminally reactive diisocyanate groups, and
i) internal polysiloxane groups; and
ii) internal polyether and polycarbonate groups; and
b) reacting the prepolymer with a chain extender to yield a polyurethane elastomeric composition,
wherein the polyether groups in the prepolymer, are provided by reaction of a polyether macrodiol of the formula:

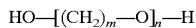

$$HO-[(CH_2)_m-O]_n-H$$

wherein
m is an integer of 4 or more;
n is an integer of from 20 to 50, and
wherein the polysiloxane is from about 60–98 wt-% of the soft segment, and the polyether and the polycarbonate is from about 2–40 wt-% of the soft segment.

34. The process of claim 33 wherein the prepolymer is reacted with the chain extender in proportions such that the hard segment is from about 30 wt. % to about 60 wt. % of the polyurethane elastomeric composition, and the soft segment is from about 40 wt. % to about 70 wt. % of the polyurethane elastomeric composition.

35. The process of claim 33 wherein the prepolymer is reacted with the chain extender in proportions such that the hard segment is from about 30 wt. % to about 50 wt. % of the polyurethane elastomeric composition.

36. The process of claim 33 wherein the prepolymer is formed by reacting about 10 wt. % to about 30 wt. % of a combination of at least one polyether macrodiol and at least one polycarbonate macrodiol, with a diisocyanate.

37. The process of claim 33 wherein the prepolymer is formed from about 70 wt. % to about 90 wt. % of at least one polysiloxane macrodiol.

38. The process of claim 33 wherein the prepolymer is formed from (a) about 10 wt. % to about 30 wt. % of a combination of at least one polyether macrodiol and at least one polycarbonate macrodiol; and (b) from about 70 wt. % to about 90 wt. % of at least one polysiloxane macrodiol.

39. The process of claim 38 wherein the polysiloxane macrodiol is polydimethylsiloxane.

40. The process of claim 39 wherein the molecular weight of the polysiloxane macrodiol is about 200 to about 6000.

41. The process of claim 40 wherein the molecular weight of the polysiloxane macrodiol is about 400 to about 1500.

42. The process of claim 33 wherein the polyether macrodiol is polytetramethylene oxide, polypentamethylene oxide, polyhexamethylene oxide, polyheptamethylene oxide, polyoctamethylene oxide, or polydecamethylene oxide.

43. The process of claim 36 wherein the polycarbonate macrodiol is a poly(alkylene carbonate), a polycarbonate prepared by reacting an alkylene carbonate with an alkane diol, or a silicon-based polycarbonate.

* * * * *

UNITED STATES PATENT AND TRADEMARK OFFICE
CERTIFICATE OF CORRECTION

PATENT NO.    : 6,627,724 B2
DATED         : September 30, 2003
INVENTOR(S)   : Meijs et al.

It is certified that error appears in the above-identified patent and that said Letters Patent is hereby corrected as shown below:

<u>Title page,</u>
Item [56], References Cited, OTHER PUBLICATIONS, "Okkema, A.Z., et al." reference, delete "polyethylele" and insert -- polyethylene --, therefor.
"Philips, R.A., et al." reference, delete "Mositure" and insert -- Moisture --, therefor.
"Sakurai, S., et al." reference, after "539" insert -- , --.
"Wise, D.L., et al." reference, delete "Biosenosrs" and insert -- Biosensors --, therefor.

<u>Column 1,</u>
Line 46, delete "degradations$^2$" and insert -- degradation$^2$ --, therefor.

<u>Column 4,</u>
Line 66, delete "prophylhexyl" and insert -- propylhexyl --, therefor.

<u>Column 5,</u>
Line 1, delete "6" and insert -- 6- --, therefor.
Line 19, delete "1-4" and insert -- 1,4- --, therefor.
Line 25, delete "monoor"and insert -- monomer --, therefor.

<u>Column 6,</u>
Line 17, delete "aryisulphonyl" and insert -- arylsulphonyl --, therefor.
Line 19, delete "helerocyclylamino" and insert -- heterocyclylamino --, therefor.

<u>Column 8,</u>
Line 15, delete "dimethyllin" and insert -- dimethyltin --, therefor.

<u>Column 16,</u>
Lines 18-19, delete "tetra- methylbutanediamine" and insert
-- tetramethylbutanediamine --, therefor.

<u>Column 25,</u>
Line 55, after "21" delete ",".

UNITED STATES PATENT AND TRADEMARK OFFICE
CERTIFICATE OF CORRECTION

PATENT NO. : 6,627,724 B2
DATED : September 30, 2003
INVENTOR(S) : Meijs et al.

It is certified that error appears in the above-identified patent and that said Letters Patent is hereby corrected as shown below:

Column 26,
Line 21, delete "diiocyanate" and insert -- diisocyanate --, therefor.
Line 21, delete "extruder" and insert -- extender --, therefor.
Line 63, delete "claim 19," and insert -- claim 26 --, therefor.

Signed and Sealed this

Eleventh Day of October, 2005

JON W. DUDAS
*Director of the United States Patent and Trademark Office*